(12) United States Patent
Sano et al.

(10) Patent No.: US 10,262,449 B2
(45) Date of Patent: Apr. 16, 2019

(54) INFORMATION PROCESSING APPARATUS, SYSTEM, AND METHOD FOR DISPLAYING BIO-INFORMATION OR KINETIC INFORMATION

(71) Applicant: Sony Corporation, Tokyo (JP)

(72) Inventors: Akane Sano, Tokyo (JP); Masamichi Asukai, Kanagawa (JP); Taiji Ito, Kanagawa (JP); Yoichiro Sako, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 15/946,954

(22) Filed: Apr. 6, 2018

(65) Prior Publication Data
US 2018/0232931 A1 Aug. 16, 2018

Related U.S. Application Data

(63) Continuation of application No. 15/389,979, filed on Dec. 23, 2016, now Pat. No. 9,972,116, which is a (Continued)

(30) Foreign Application Priority Data

Aug. 6, 2007 (JP) ................. 2007-204114

(51) Int. Cl.
*G06T 13/40* (2011.01)
*G16H 50/50* (2018.01)
(Continued)

(52) U.S. Cl.
CPC .............. *G06T 13/40* (2013.01); *A61B 3/113* (2013.01); *A61B 5/0006* (2013.01);
(Continued)

(58) Field of Classification Search
CPC . A61B 5/0488; A61B 5/14551; A61B 5/0476; A61B 3/113; A61B 5/0022;
(Continued)

(56) References Cited

U.S. PATENT DOCUMENTS 5,781,650 A  7/1998  Lobo et al.
6,057,856 A  5/2000  Miyashita et al.
(Continued)

FOREIGN PATENT DOCUMENTS

CN  1605974 A  4/2005
CN  1835711 A  9/2006
(Continued)

OTHER PUBLICATIONS

Healey, Jennifer et al.: "StartleCam: A Cybernetic Wearable Camera," . Digest of Papers. Second Internationi Symposium on Wearable Computers, 1998 Pittsburgh, PA USA Oct. 1920, 1998, pp. 42-49.

*Primary Examiner* — Maurice L. McDowell, Jr.
*Assistant Examiner* — Donna J. Ricks
(74) *Attorney, Agent, or Firm* — Wolf, Greenfield & Sacks, P.C.

(57) ABSTRACT

An information processing apparatus includes a bio-information obtaining unit configured to obtain bio-information of a subject; a kinetic-information obtaining unit configured to obtain kinetic information of the subject; and a control unit configured to determine an expression or movement of an avatar on the basis of the bio-information obtained by the bio-information obtaining unit and the kinetic information obtained by the kinetic-information obtaining unit and to perform a control operation so that the avatar with the determined expression or movement is displayed.

17 Claims, 18 Drawing Sheets

Related U.S. Application Data continuation of application No. 14/314,385, filed on Jun. 25, 2014, now Pat. No. 9,568,998, which is a continuation of application No. 12/221,526, filed on Aug. 4, 2008, now Pat. No. 8,797,331.

(51) Int. Cl.

| | | |
|---|---|---|
| *G06F 3/01* | (2006.01) | |
| *A61B 5/00* | (2006.01) | |
| *A61B 5/0205* | (2006.01) | |
| *A61B 5/0402* | (2006.01) | |
| *A61B 5/0476* | (2006.01) | |
| *A61B 5/0488* | (2006.01) | |
| *A61B 5/16* | (2006.01) | |
| *A61B 3/113* | (2006.01) | |
| *A61B 5/01* | (2006.01) | |
| *A61B 5/11* | (2006.01) | |
| *A61B 5/1455* | (2006.01) | |
| *G06K 9/00* | (2006.01) | |
| *G06T 7/20* | (2017.01) | |
| *G06F 19/00* | (2018.01) | |
| *A61B 5/024* | (2006.01) | |
| *A61B 5/053* | (2006.01) | |
| *A61B 5/08* | (2006.01) | |
| *A61B 5/021* | (2006.01) | |
| *A61B 5/026* | (2006.01) | |

(52) U.S. Cl.
CPC .......... *A61B 5/0008* (2013.01); *A61B 5/0022* (2013.01); *A61B 5/01* (2013.01); *A61B 5/02055* (2013.01); *A61B 5/0402* (2013.01); *A61B 5/0476* (2013.01); *A61B 5/0488* (2013.01); *A61B 5/1118* (2013.01); *A61B 5/1123* (2013.01); *A61B 5/14551* (2013.01); *A61B 5/165* (2013.01); *A61B 5/4266* (2013.01); *A61B 5/742* (2013.01); *A61B 5/744* (2013.01); *G06F 3/015* (2013.01); *G06F 19/00* (2013.01); *G06K 9/00335* (2013.01); *G06T 7/20* (2013.01); *G16H 50/50* (2018.01); *A61B 5/021* (2013.01); *A61B 5/024* (2013.01); *A61B 5/026* (2013.01); *A61B 5/0533* (2013.01); *A61B 5/08* (2013.01); *Y10S 345/95* (2013.01)

(58) Field of Classification Search
CPC ....... A61B 5/0006; A61B 5/0008; A61B 5/01; A61B 5/02055; A61B 5/1123; A61B 5/0402; A61B 5/1118; A61B 5/4266; A61B 5/742; A61B 5/08; A61B 5/021; A61B 5/0533; A61B 5/024; A61B 5/026; A61B 5/744; A61B 5/165; G06T 13/40; G06T 7/20; G06K 9/00335; G06F 19/00; G06F 3/015; G16H 50/50; Y10S 345/95
See application file for complete search history.

(56) References Cited

U.S. PATENT DOCUMENTS

| | | |
|---|---|---|
| 6,072,496 A | 6/2000 | Guenter et al. |
| 6,091,546 A | 7/2000 | Spitzer |
| 6,181,371 B1 | 1/2001 | Maguire, Jr. |
| 6,272,231 B1 | 8/2001 | Maurer et al. |
| 6,293,904 B1 | 9/2001 | Blazey et al. |
| 6,362,817 B1 | 3/2002 | Powers et al. |
| 6,466,862 B1 | 10/2002 | Dekock et al. |
| 6,549,231 B1 | 4/2003 | Matsui |
| 6,549,913 B1 | 4/2003 | Murakawa |
| 6,585,521 B1 | 7/2003 | Obrador |
| 6,629,104 B1 | 9/2003 | Panilski et al. |
| 6,774,885 B1 | 8/2004 | Even-Zohar |
| 7,073,129 B1 | 7/2006 | Robarts et al. |
| 7,085,648 B2 | 8/2006 | Ishiguro |
| 7,183,909 B2 | 2/2007 | Miyajima |
| 7,286,753 B2 | 10/2007 | Yamasaki |
| 7,876,374 B2 | 1/2011 | Sako et al. |
| 8,009,219 B2 | 8/2011 | Sako et al. |
| 8,126,220 B2 | 2/2012 | Greig |
| 8,473,544 B2 | 6/2013 | Sako et al. |
| 8,503,086 B2 | 8/2013 | French et al. |
| 8,687,925 B2 | 4/2014 | Sano et al. |
| 8,797,331 B2 | 8/2014 | Sano et al. |
| 8,872,941 B2 | 10/2014 | Asukai et al. |
| 8,949,324 B2 | 2/2015 | Sako et al. |
| 9,568,998 B2 | 2/2017 | Sano et al. |
| 2001/0005230 A1 | 6/2001 | Ishikawa |
| 2001/0040590 A1 | 11/2001 | Abbott et al. |
| 2002/0007105 A1 | 1/2002 | Prabhu et al. |
| 2002/0054174 A1 | 5/2002 | Abbott et al. |
| 2002/0101619 A1 | 8/2002 | Tsubaki et al. |
| 2002/0128541 A1 | 9/2002 | Kim et al. |
| 2003/0009078 A1 | 1/2003 | Fedorovskaya et al. |
| 2003/0011684 A1 | 1/2003 | Narayanaswami et al. |
| 2003/0117505 A1 | 6/2003 | Sasaki et al. |
| 2003/0118974 A1 | 6/2003 | Obrador |
| 2003/0128389 A1 | 7/2003 | Matraszek et al. |
| 2003/0165270 A1 | 9/2003 | Endrikhovski et al. |
| 2003/0225516 A1 | 12/2003 | Dekock et al. |
| 2003/0235411 A1 | 12/2003 | Morikawa et al. |
| 2004/0101178 A1 | 5/2004 | Fedorovskaya et al. |
| 2004/0101212 A1 | 5/2004 | Fedorovskaya et al. |
| 2004/0174443 A1 | 9/2004 | Simske |
| 2004/0201692 A1 | 10/2004 | Parulski et al. |
| 2004/0210661 A1 | 10/2004 | Thompson |
| 2004/0221224 A1 | 11/2004 | Blattner et al. |
| 2004/0243567 A1 | 12/2004 | Levy |
| 2004/0267440 A1 | 12/2004 | Dekock et al. |
| 2005/0054381 A1 | 3/2005 | Lee et al. |
| 2005/0083333 A1 | 4/2005 | Gordon |
| 2005/0088297 A1 | 4/2005 | Miyajima |
| 2005/0124851 A1 | 6/2005 | Patton et al. |
| 2005/0149467 A1 | 7/2005 | Ono et al. |
| 2005/0171997 A1 | 8/2005 | Seo et al. |
| 2005/0181347 A1 | 8/2005 | Barnes et al. |
| 2005/0195277 A1 | 9/2005 | Yamasaki |
| 2005/0206583 A1 | 9/2005 | Lemelson et al. |
| 2005/0248469 A1 | 11/2005 | Dekock et al. |
| 2005/0248852 A1 | 11/2005 | Yamasaki |
| 2005/0250996 A1 | 11/2005 | Shirai et al. |
| 2005/0289582 A1 | 12/2005 | Tavares et al. |
| 2006/0010240 A1 | 1/2006 | Chuah |
| 2006/0012690 A1 | 1/2006 | Nakamura et al. |
| 2006/0074546 A1 | 4/2006 | Dekock et al. |
| 2006/0115130 A1 | 6/2006 | Kozlay |
| 2006/0134585 A1 | 6/2006 | Adamo-Villani et al. |
| 2006/0143647 A1 | 6/2006 | Bill |
| 2006/0217598 A1 | 9/2006 | Miyajima et al. |
| 2006/0256382 A1 | 11/2006 | Matraszek et al. |
| 2007/0067273 A1 | 3/2007 | Willcock |
| 2007/0074114 A1 | 3/2007 | Adjali et al. |
| 2007/0113181 A1 | 5/2007 | Blattner et al. |
| 2007/0132765 A1 | 6/2007 | Lee et al. |
| 2007/0172155 A1 | 7/2007 | Guckenberger |
| 2007/0184855 A1 | 8/2007 | Klassen et al. |
| 2007/0185390 A1 | 8/2007 | Perkins et al. |
| 2007/0201767 A1 | 8/2007 | Fujita |
| 2007/0285560 A1 | 12/2007 | Perlman |
| 2008/0020361 A1 | 1/2008 | Kron et al. |
| 2008/0045804 A1 | 2/2008 | Williams |
| 2008/0052242 A1 | 2/2008 | Merritt et al. |
| 2008/0091512 A1 | 4/2008 | Marci et al. |
| 2008/0107361 A1 | 5/2008 | Asukai |
| 2008/0129839 A1 | 6/2008 | Asukai |
| 2008/0136930 A1 | 6/2008 | Nagai |
| 2008/0146302 A1 | 6/2008 | Olsen et al. |
| 2008/0158232 A1 | 7/2008 | Shuster |
| 2008/0181513 A1 | 7/2008 | Almeida |
| 2008/0187186 A1 | 8/2008 | Togashi |

(56) References Cited

U.S. PATENT DOCUMENTS

| | | |
|---|---|---|
| 2008/0188310 A1 | 8/2008 | Murdock |
| 2008/0215974 A1 | 9/2008 | Harrison et al. |
| 2008/0253695 A1 | 10/2008 | Sano et al. |
| 2008/0259199 A1 | 10/2008 | Sako et al. |
| 2008/0273765 A1 | 11/2008 | Tsujimura |
| 2009/0040231 A1 | 2/2009 | Sano et al. |
| 2009/0124922 A1 | 5/2009 | Milgramm et al. |
| 2009/0279792 A1 | 11/2009 | Obdrzalek et al. |
| 2010/0063997 A1 | 3/2010 | Sako et al. |
| 2010/0220037 A1 | 9/2010 | Sako et al. |
| 2010/0302142 A1 * | 12/2010 | French ............... A63B 24/0003 345/156 |
| 2013/0335352 A1 | 12/2013 | Sako et al. |
| 2014/0306884 A1 | 10/2014 | Sano et al. |
| 2015/0002697 A1 | 1/2015 | Asukai et al. |
| 2015/0022427 A1 | 1/2015 | Sako et al. |
| 2017/0109919 A1 | 4/2017 | Sano et al. |

FOREIGN PATENT DOCUMENTS

| | | | |
|---|---|---|---|
| CN | 1945984 A | | 4/2007 |
| CN | 1991692 A | | 7/2007 |
| EP | 1246136 A2 | | 3/2002 |
| EP | 1324274 A | | 7/2003 |
| EP | 1503376 A2 | | 2/2005 |
| EP | 1571634 A1 | | 2/2005 |
| EP | 1522256 A1 | | 4/2005 |
| EP | 1593964 A | | 11/2005 |
| EP | 1656880 A | | 5/2006 |
| EP | 1708150 A | | 10/2006 |
| GB | 2394852 A | | 5/2004 |
| GB | 2403366 A | | 12/2004 |
| JP | 09-065188 A | | 3/1997 |
| JP | 10-113343 A | | 5/1998 |
| JP | 2002-169809 A | | 6/2002 |
| JP | 2003-079591 A | | 3/2003 |
| JP | 2004-049309 A | | 2/2004 |
| JP | 2004-178593 A | | 6/2004 |
| JP | 2004-194996 A | | 7/2004 |
| JP | 2004-537193 A | | 12/2004 |
| JP | 2004-538679 A | | 12/2004 |
| JP | 2004-538681 A | | 12/2004 |
| JP | 2005-064839 A | | 3/2005 |
| JP | 2005-124909 A | | 5/2005 |
| JP | 2005-141281 A | | 6/2005 |
| JP | 2005-172851 A | | 6/2005 |
| JP | 2005-195425 A | | 7/2005 |
| JP | 2005-250977 A | | 9/2005 |
| JP | 2005-260892 A | | 9/2005 |
| JP | 2005-337863 A | | 12/2005 |
| JP | 2005-341604 A | | 12/2005 |
| JP | 2006-034803 A | | 2/2006 |
| JP | 2006-080644 A | | 3/2006 |
| JP | 2006-086823 A | | 3/2006 |
| JP | 2006-087829 A | | 4/2006 |
| JP | 2006-126891 A | | 5/2006 |
| JP | 2006-146630 A | | 6/2006 |
| JP | 2006-172146 A | | 6/2006 |
| JP | 2007-011391 A | | 1/2007 |
| JP | 2007-041964 A | | 2/2007 |
| JP | 2007-081681 A | | 3/2007 |
| WO | WO 99/49656 A1 | | 9/1999 |
| WO | WO 01/43104 A1 | | 6/2001 |
| WO | WO 2004/017249 A2 | | 2/2004 |

* cited by examiner

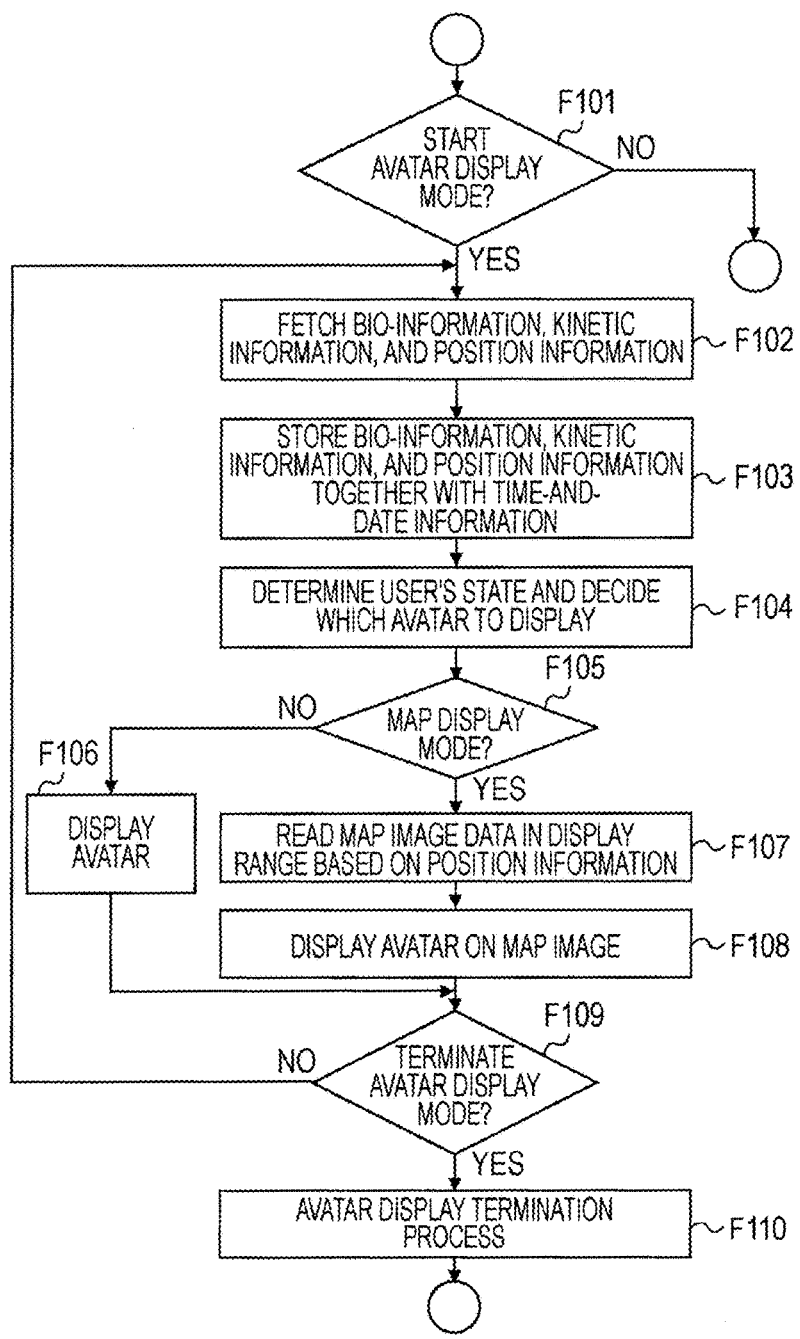

FIG. 6A

| TIME AND DATE | POSITION INFORMATION | BIO-INFORMATION | KINETIC INFORMATION |
|---|---|---|---|
| 7/8/2007 12:05 | PL1 | L1 | M1 |
| 7/8/2007 12:10 | PL2 | L2 | M2 |
| 7/8/2007 12:15 | PL3 | L3 | M3 |
| ⋮ | ⋮ | ⋮ | ⋮ |

FIG. 6B

| TIME AND DATE | POSITION INFORMATION | BIO-INFORMATION | KINETIC INFORMATION | AVATAR-RELATED INFORMATION |
|---|---|---|---|---|
| 7/8/2007 12:05 | PL1 | L1 | M1 | C1 |
| 7/8/2007 12:10 | PL2 | L2 | M2 | C2 |
| 7/8/2007 12:15 | PL3 | L3 | M3 | C3 |
| ⋮ | ⋮ | ⋮ | ⋮ | ⋮ |

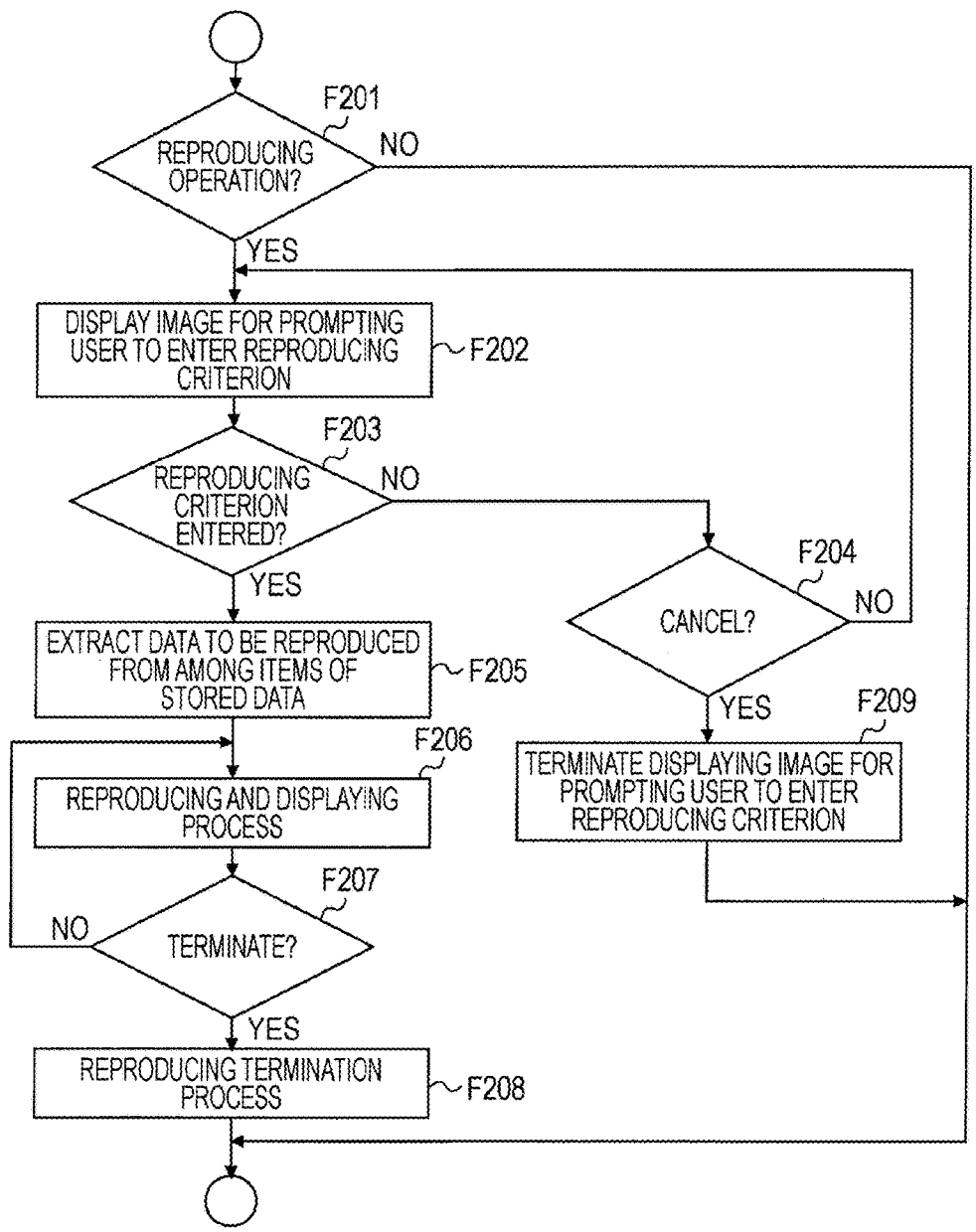

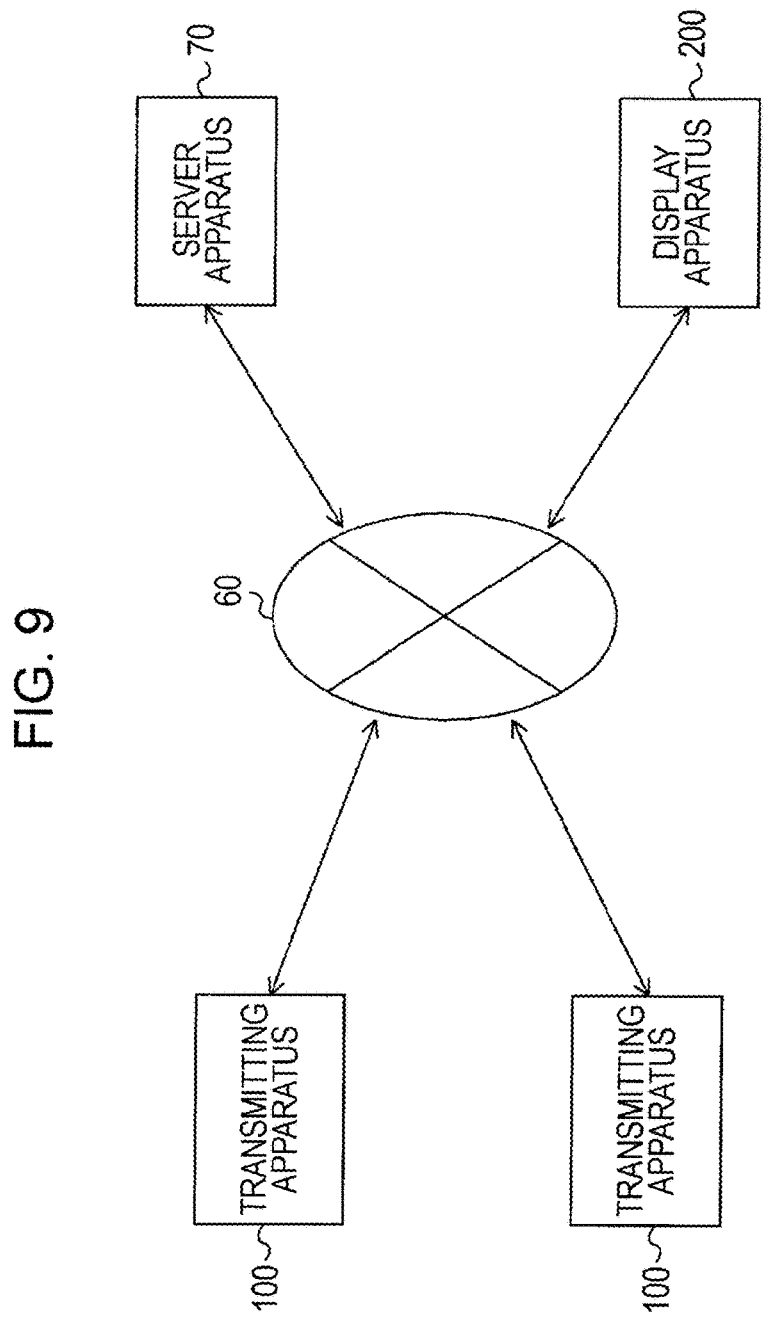

FIG. 15

| USER ID | STORED DATA | | | | | | | | | | | |
|---|---|---|---|---|---|---|---|---|---|---|---|---|
| UID 1 | L | M | PL | Date | L | M | PL | Date | | | | |
| UID 2 | L | M | PL | Date | | | | | | | | |
| UID 3 | L | M | PL | Date | L | M | PL | Date | L | M | PL | Date |
| ⋮ | | | | | | | | | | | | |

INFORMATION PROCESSING APPARATUS, SYSTEM, AND METHOD FOR DISPLAYING BIO-INFORMATION OR KINETIC INFORMATION

CROSS REFERENCES TO RELATED APPLICATIONS

This application is a continuation of and claims the benefit under 35 U.S.C. § 120 of U.S. patent application Ser. No. 15/389,979, titled "INFORMATION PROCESSING APPARATUS, SYSTEM, AND METHOD FOR DISPLAYING BIO-INFORMATION OR KINETIC INFORMATION," filed on Dec. 23, 2016 which is a continuation of and claims the benefit under 35 U.S.C. § 120 of U.S. patent application Ser. No. 14/314,385, titled "INFORMATION PROCESSING APPARATUS, SYSTEM, AND METHOD FOR DISPLAYING BIO-INFORMATION OR KINETIC INFORMATION," filed on Jun. 25, 2014, which is a continuation of and claims the benefit under 35 U.S.C. § 120 of U.S. patent application Ser. No. 12/221,526, titled "INFORMATION PROCESSING APPARATUS, SYSTEM, AND METHOD THEREOF," filed on Aug. 4, 2008, which claims priority to and contains subject matter related to Japanese Patent Application JP 2007-204114, filed in the Japanese Patent Office on Aug. 6, 2007, all of which are hereby incorporated herein by reference in their entireties.

BACKGROUND OF THE INVENTION

1. Field of the Invention

The present invention relates to information processing apparatuses, systems, and methods thereof, and more particularly, to the technique of displaying avatars in accordance with bio-information and kinetic information of a user and other persons.

2. Description of the Related Art

Japanese Unexamined Patent Application Publication No. 2006-126891 discloses the technique relating to transmitting bio-information over a network.

Japanese Unexamined Patent Application Publication Nos. 2006-34803, 2006-87829, 2003-79591, and 2004-194996 each describe an apparatus for displaying various types of bio-information.

Japanese Unexamined Patent Application Publication No. 2007-11391 discloses a map generating system of extracting a user's subjective information and mapping the information on a map.

SUMMARY OF THE INVENTION

No systems of easily and clearly presenting bio-information and kinetic information of a user and other persons or situations estimated from these items of information have been proposed yet.

In particular, detected results of bio-information such as the heart rate or blood pressure have generally been shown using numerals or graphs. However, this is targeted at professionally trained people with knowledge in the medical field and is not a simple way of presenting such information.

It is desirable to display bio-information and kinetic information of a user and other persons or situations estimated from these items of information in a manner that enables general people other than professionals to easily understand these items of information or situations estimated therefrom, thereby creating various applications.

An information processing apparatus according to an embodiment of the present invention includes the following elements: bio-information obtaining means for obtaining bio-information of a subject (e.g., a person); kinetic-information obtaining means for obtaining kinetic information of the subject; and control means for determining an expression or movement of an avatar on the basis of the bio-information obtained by the bio-information obtaining means and the kinetic information obtained by the kinetic-information obtaining means and performing a control operation so that the avatar with the determined expression or movement is displayed.

The bio-information obtaining means may be a bio-information detecting unit configured to detect bio-information, and the kinetic-information obtaining means may be a kinetic-information detecting unit configured to detect kinetic information. That is, the information processing apparatus itself has the function of detecting bio-information and kinetic information.

The bio-information obtaining means and the kinetic-information obtaining means may be communication units configured to receive bio-information and kinetic information, respectively, from an external apparatus. That is, the bio-information obtaining means and the kinetic-information obtaining means may obtain bio-information and kinetic information, respectively, using a communication function.

The information processing apparatus may further include display means for displaying an image. The control means may perform a control operation so that the avatar is displayed on the display means.

The information processing apparatus may further include position-information obtaining means for obtaining position information; and map-image obtaining means for obtaining map image data. The control means may control, on the basis of the position information obtained by the position-information obtaining means, the map-image obtaining means to obtain map image data to display a map image and may perform a control operation so that the avatar is displayed at a position in accordance with the position information on the map image.

The control means may perform, when the bio-information obtaining means and the kinetic-information obtaining means obtain bio-information and kinetic information, respectively, a display control operation to display the avatar with the expression or movement determined on the basis of the bio-information and the kinetic information. That is, the avatar is displayed in real-time on the basis of the just obtained bio-information and kinetic information.

The information processing apparatus may further include saving means for saving information. The control means may cause, when the bio-information obtaining means and the kinetic-information obtaining means obtain bio-information and kinetic information, respectively, the saving means to save the obtained bio-information and kinetic information or avatar-related information indicating the expression or movement of the avatar, the expression or movement being determined on the basis of the obtained bio-information and kinetic information.

In that case, the control means may read the bio-information and the kinetic information or the avatar-related information from the saving means under a predetermined condition and perform a display control operation so that the avatar is displayed using the read bio-information and kinetic information or the read avatar-related information.

That is, the avatar can be displayed on the basis of bio-information and kinetic information obtained in the past.

The bio-information may include information indicating at least one of the pulse rate, heart rate, electrocardiographic signal, electromyogram, breathing (e.g., the rate and depth of breathing and the amount of ventilation), perspiration, galvanic skin response (GSR), blood pressure, saturation of pulse oximetry oxygen (SpO2), skin surface temperature, brain wave (e.g., α wave, β wave, θ wave, and δ wave information), blood flow change (change in the flow of blood such as cerebral blood or peripheral blood detected using near-infrared spectroscopy), temperature, and status of eyes (status of pupils, movement of eyes, blink, etc.).

The kinetic information may be information indicating at least one of a still state, a walking state, a running state, an exercising state (e.g., shaking or jumping), and movement of a body element (e.g., the head, arm, leg, hand, or finger).

According to another embodiment of the present invention, there is provided an information processing system including a transmitting apparatus; and an information processing apparatus. The transmitting apparatus includes bio-information detecting means for detecting bio-information of a subject (e.g., a person who is wearing the transmitting apparatus), kinetic-information detecting means for detecting kinetic information of the subject, and transmitting means for transmitting and outputting the bio-information detected by the bio-information detecting means and the kinetic information detected by the kinetic-information detecting means. The information processing apparatus includes communication means for communicating information, and control means for causing the communication means to receive bio-information and kinetic information, determining an expression or movement of an avatar on the basis of the bio-information and kinetic information received by the communication means, and performing a control operation so that the avatar with the determined expression or movement is displayed.

The information processing system may further include a server apparatus including storage means for storing bio-information and kinetic information. The transmitting means of the transmitting apparatus may transmit the bio-information and the kinetic information to the server apparatus. The server apparatus may store the transmitted bio-information and kinetic information in the storage means. The communication means of the information processing apparatus may receive the bio-information and kinetic information stored in the storage means of the server apparatus.

Alternatively, the communication means of the information processing apparatus may receive avatar-related information indicating the expression or movement of the avatar, the expression or movement being determined on the basis of the bio-information and kinetic information stored in the storage means of the server apparatus.

According to another embodiment of the present invention, there is provided an information processing method including the steps of obtaining bio-information of a subject (e.g., a person); obtaining kinetic information of the subject; determining an expression or movement of an avatar on the basis of the obtained bio-information and kinetic information; and performing a control operation so that the avatar with the determined expression or movement is displayed.

According to the embodiments of the present invention, an avatar with an expression or movement determined on the basis of bio-information and kinetic information is displayed for a user. The avatar is assumed to be, for example, an image of a personified animal or object or an animated image of a person. By determining the expression or movement of the avatar on the basis of bio-information and kinetic information, the person's state such as the state of movement, health, or emotion can be represented.

According to the embodiments of the present invention, the state of a person (such as a user or another person) serving as a subject can be represented using the expression or movement of a displayed avatar. Accordingly, a person having no technical background can easily know the person's or another person's state. By displaying an image representing the state of a person, various applications can be realized, including an application for managing the person's health, a communications application, and an application for enhancing the feeling of delight at viewing images displayed on various apparatuses.

BRIEF DESCRIPTION OF THE DRAWINGS

FIG. 4 is a flowchart of a process of displaying an avatar according to the embodiment;

FIGS. 6A and 6B are illustrations of recording states of bio-information and the like according to the embodiment;

FIG. 7 is a flowchart of a process of reproducing and displaying an avatar according to the embodiment;

FIG. 9 is a diagram of an information processing system according to the embodiment;

FIG. 15 is an illustration of storage states of bio-information and the like in the server apparatus according to the embodiment;

DESCRIPTION OF THE PREFERRED EMBODIMENTS

Figure 1:
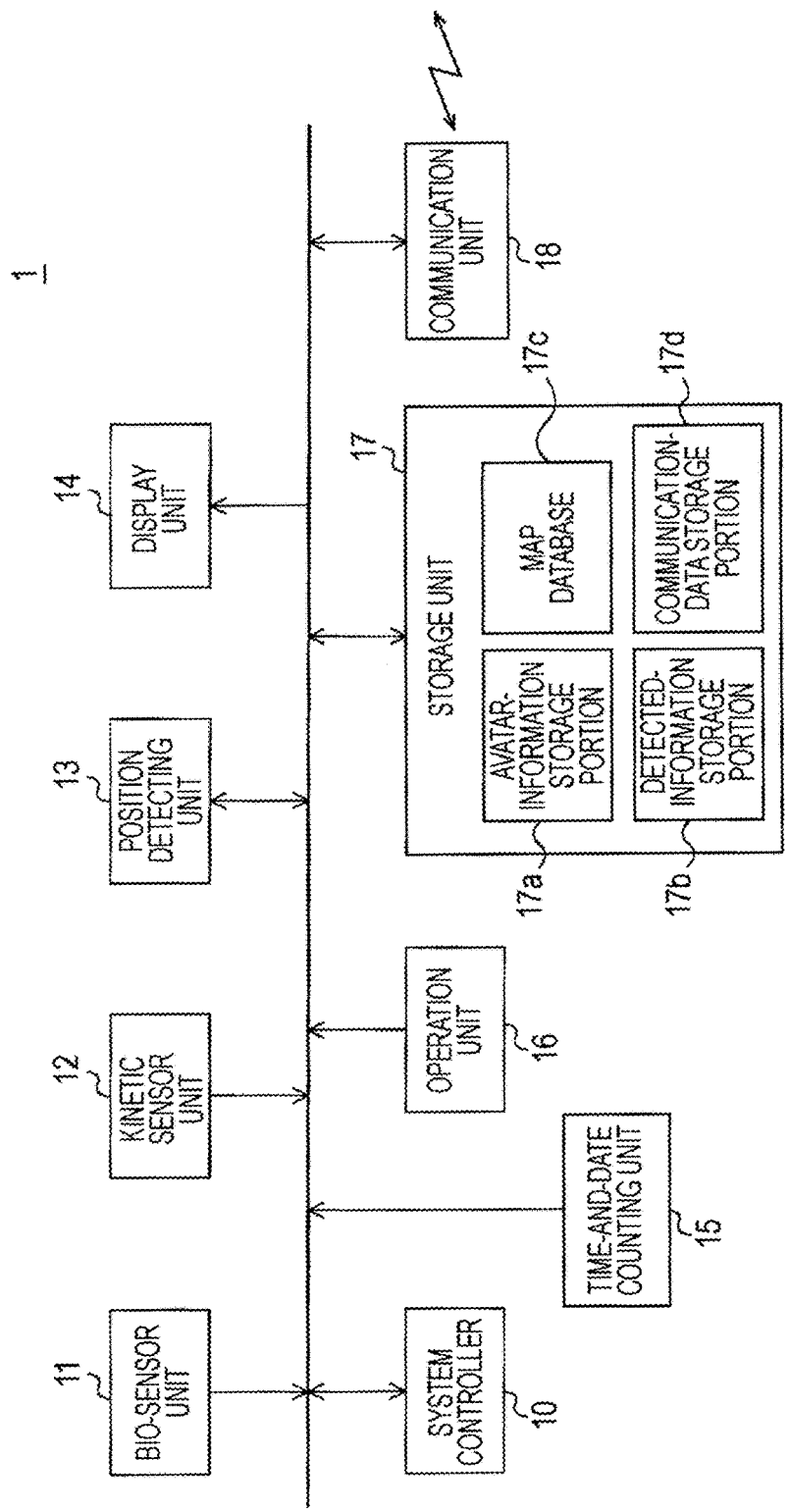
FIG. 1 is a block diagram of an information display apparatus according to an embodiment of the present invention.

Embodiments of the present invention are described below. Descriptions are given in the following order:
1. Displaying Avatar Based on User's Bio- and Kinetic Information 1-1 Structure of Information Display Apparatus
1-2 Process of Displaying Avatar in Real-Time
1-3 Process of Reproducing and Displaying Avatars as State History
2. Displaying Avatar Based on Another Person's Bio- and Kinetic Information
2-1 System Configuration
2-2 Structure of Transmitting Apparatus
2-3 Structure of Server Apparatus
2-4 Structure of Display Apparatus
2-5 System Operation for Displaying Avatar
3. Displaying Avatars Based on User's and Another Person's Bio- and Kinetic Information
4. Advantages and Modifications of Embodiment

1. Displaying Avatar Based on User's Bio- and Kinetic Information 1-1 Structure of Information Display Apparatus Referring to FIG. 1, the structure of an information display apparatus 1 is described. The information display apparatus 1 is an apparatus carried by a user. The information display apparatus 1 displays, on its display screen, an avatar based on bio- and kinetic information of the user carrying the information display apparatus 1.

The information display apparatus 1 may be, for example, an apparatus with a glasses-type display and worn on the head of the user. Alternatively, the information display apparatus 1 may be a watch-type apparatus and worn on the wrist of the user. Alternatively, the information display apparatus 1 may be an apparatus having a shape and size suitable for being carried by the user, such as a cellular phone or a personal digital assistant (PDA). Further, the information display apparatus 1 may be provided as an internal function which is included in a cellular phone or a PDA and serves as the information display apparatus 1.

The information display apparatus 1 includes a system controller 10, a bio-sensor unit 11, a kinetic sensor unit 12, a position detecting unit 13, a display unit 14, a time-and-date counting unit 15, an operation unit 16, a storage unit 17, and a communication unit 18.

The system controller 10 is implemented by, for example, a microcomputer including a central processing unit (CPU), a read-only memory (ROM), a random access memory (RAM), a non-volatile memory, and an interface. The system controller 10 controls the overall information display apparatus 1.

On the basis of an internal operation program, the system controller 10 controls the components of the information display apparatus 1 to perform a display operation based on bio- and kinetic information.

The bio-sensor unit 11 detects a user's bio-information. Bio-information includes, for example, the pulse rate, heart rate, electrocardiographic signal, electromyogram, breathing (e.g., the rate and depth of breathing and the amount of ventilation), perspiration, galvanic skin response (GSR), blood pressure, saturation of pulse oximetry oxygen (SpO2), skin surface temperature, brain wave (e.g., $\alpha$ wave, $\beta$ wave, $\theta$ wave, and $\delta$ wave information), blood flow change (change in the flow of blood such as cerebral blood or peripheral blood detected using near-infrared spectroscopy), temperature, and status of eyes (status of pupils, movement of eyes, blink, etc.).

For example, the GSR, temperature, skin surface temperature, electrocardiogram response, electromyogram heart rate, pulse rate, blood flow, blood pressure, brain wave, or perspiration can be detected using, for example, a sensor in contact with the skin of a subject. The brain wave can be detected using a sensor in contact with and worn on the head of a subject.

A sensor that detects the eyes of a user can be implemented by, for example, an imaging unit that captures an image of the user's eyes. In this case, the image of the user's eyes captured by the imaging unit is analyzed to detect the viewing direction, focal length, dilation of the pupils, the fundus pattern, and the movement of the eyelids. Alternatively, the sensor can be implemented by a light-emitting unit that emits light to the eyes of the user and a light-receiving unit that receives light reflected from the eyes. For example, the thickness of the crystalline lens of the user can be detected from a received light signal.

The bio-sensor unit 11 outputs detection result information obtained by these necessary sensors to the system controller 10.

The kinetic sensor unit 12 detects the user's kinetic information. Kinetic information includes, for example, information indicating the user's state, such as a still, walking, or running state, information indicating an exercising state (shaking, jumping, walking/running rhythm, the center of gravity, etc.), or information indicating the movement of the user's body elements including the head, arms, legs, hands, and fingers.

These items of kinetic information can be detected using an acceleration sensor, a gyro (angular-velocity sensor), a vibration sensor, and the like. That is, when an acceleration sensor or a gyro is provided, for example, the movement of the entire body, head, neck, arms, and legs can be detected as signals in accordance with the user's movement. When detecting the movement of arms or legs, an acceleration sensor or a gyro may be worn on the user's arms or legs.

The kinetic sensor unit 12 outputs detection result information obtained by the acceleration sensor and the like to the system controller 10.

The position detecting unit 13 is, for example, a Global Positioning System (GPS) receiver. The GPS receiver receives radio waves from GPS satellites and outputs latitude and longitude information indicating the current position to the system controller 10.

Alternatively, the position detecting unit 13 may use wireless fidelity (WiFi) or a position information service provided by a cellular phone company.

The time-and-date counting unit 15 constantly performs a time-and-date counting operation and counts the seconds, minutes, hours, days, months, and years.

The operation unit 16 is provided as an operation unit including keys and/or a dial used by the user of the information display apparatus 1 to enter various operations. Alternatively, the display unit 14 includes a touch panel, and this touch panel may be touched and operated as the operation unit 16.

For example, the operation unit 16 may be operated to enter operations such as power on/off operations, display-related operations (e.g., operations to select a display mode or perform display adjustment), various setting operations, and further, an operation to display a state history of the past, which is described later.

The system controller 10 performs a necessary control process based on operation information from the operation unit 16.

Since the information display apparatus 1 in this example includes the bio-sensor unit 11 and the kinetic sensor unit 12, the user's intended actions may be detected from bio- and kinetic information detected by the bio-sensor unit 11 and the kinetic sensor unit 12, and the system controller 10 may determine that the user's intended actions as entered operation information.

For example, when the user taps the user's fingers on the information display apparatus 1, the acceleration sensor or vibration sensor of the kinetic sensor unit 12 may detect this tapping, and the system controller 10 may recognize this tapping as a user operation.

Alternatively, when the user rotates the head or shakes the neck, the acceleration sensor or angular-velocity sensor may detect this rotation or shaking, and the system controller 10 may recognize this rotation or shaking as a user operation.

Alternatively, the bio-sensor unit 11 may detect the movement of the user's eyes, and the system controller 10 may recognize this movement (change in the viewing direction or blinking) which serves as the user's intended action as a user operation.

The communication unit 18 performs data transmission/reception with an external apparatus. The communication unit 18 is only necessary to be connected to a network via cable or wirelessly and to perform communication. For example, the communication unit 18 may perform communication over a network in a system shown in FIG. 9, which is described later, or may directly communicate data with another apparatus.

Under control of the system controller 10, the storage unit 17 records (saves) various items of data and reproduces (reads) recorded data.

The storage unit 17 may be implemented by a fixed memory, such as a RAM or a flash memory, or may be implemented by, for example, a hard disk drive (HDD).

Alternatively, the storage unit 17 may be implemented by, besides an internal recording medium, a read/write drive corresponding to recording media such as portable recording media, such as a memory card including a fixed memory, an optical disk, a magneto-optical disk, and a hologram memory.

Alternatively, the storage unit 17 may include both types, namely, an internal-type memory such as a fixed memory or HDD and a read/write drive corresponding to portable recording media.

In this example, the storage unit 17 includes storage areas serving as, more particularly, an avatar-information storage portion 17a, a detected-information storage portion 17b, a map database 17c, and a communication-data storage portion 17d.

The avatar-information storage portion 17a stores items of image data serving as avatars to be displayed. For example, the avatar-information storage portion 17a stores various items of image data indicating the design of each avatar and the expression and/or movement of each avatar.

Figure 3C:
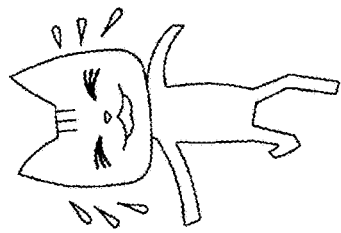
FIGS. 3A to 3F are illustrations of avatars according to the embodiment.
Figure 3F:
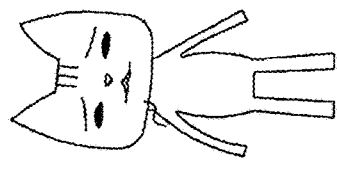
Figure 3B:
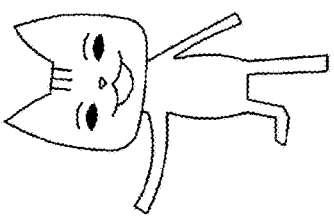
Figure 3E:
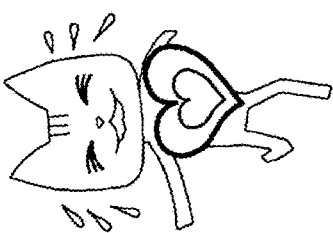
Figure 3A:
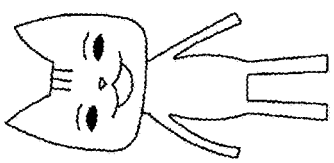
Figure 3D:
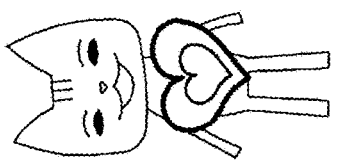

For example, FIGS. 3A to 3F illustrate examples of avatars. FIGS. 3A, 3B and 3C illustrate exemplary images representing a still state, a walking state, and a running state, respectively, using movements and expressions. FIG. 3D illustrates an exemplary image representing a state in which the avatar is still and has a fast pulse using a heart symbol. FIG. 3E illustrates an exemplary image representing a state in which the avatar is running and has a fast pulse using a heart symbol. FIG. 3F illustrates an exemplary image representing a state in which the avatar is depressed using an expression.

The avatar-information storage portion 17a stores items of image data representing, for example, the foregoing avatars and movements and expressions of the avatars.

The detected-information storage portion 17b stores bio-information detected by the bio-sensor unit 11, kinetic information detected by the kinetic sensor unit 12, and position information detected by the position detecting unit 13. For example, under control of the system controller 10, the detected-information storage portion 17b stores these items of information, together with time-and-date information counted by the time-and-date counting unit 15, at constant time intervals. That is, the detected-information storage portion 17b stores a history of the user's bio- and kinetic information and position information.

The map database 17c stores map images for displaying maps and other necessary information.

The communication-data storage portion 17d is used as a buffer or storage of data transmitted from/received by the communication unit 18.

The display unit 14 includes a display panel portion implemented by, for example, a liquid crystal panel or an organic electroluminescent (EL) panel and a display drive portion for driving the display panel portion. The display drive portion is implemented by a pixel drive circuit for displaying an image represented by supplied image data on the display panel portion. The pixel drive circuit applies drive signals based on video signals to pixels arranged in a matrix in the display panel portion at predetermined horizontal and vertical drive timings and causes the pixels to display an image.

Under control of the system controller 10, the display unit 14 causes the display panel portion to perform a predetermined display operation. More particularly in this example, the system controller 10 supplies avatar data based on bio- and kinetic information to the display unit 14 and causes the display unit 14 to display an avatar. That is, the displayed avatar is illustrated in one of FIGS. 3A to 3F. The system controller 10 decides which avatar to display on the basis of the bio- and kinetic information and supplies the decided avatar to the display unit 14.

In some cases, the system controller 10 may cause the display unit 14 to display a map image using map image data stored in the map database 17c.

It is preferable that the foregoing information display apparatus 1 be constructed as a small and light-weight apparatus so that the user can wear the apparatus. Depending on the details of bio-information to be detected, it is preferable that the information display apparatus 1 be constructed as, for example, a wrist watch type, glasses type, headset type, hat type, helmet type, or glove type apparatus or as clothing including the apparatus. In particular, the information display apparatus 1 is preferably constructed so that a part (the bio-sensor unit 11) of the information display apparatus 1 can be in contact with an appropriate body part, such as the skin or head of a subject, in accordance with details of information to be detected.

Figure 2:
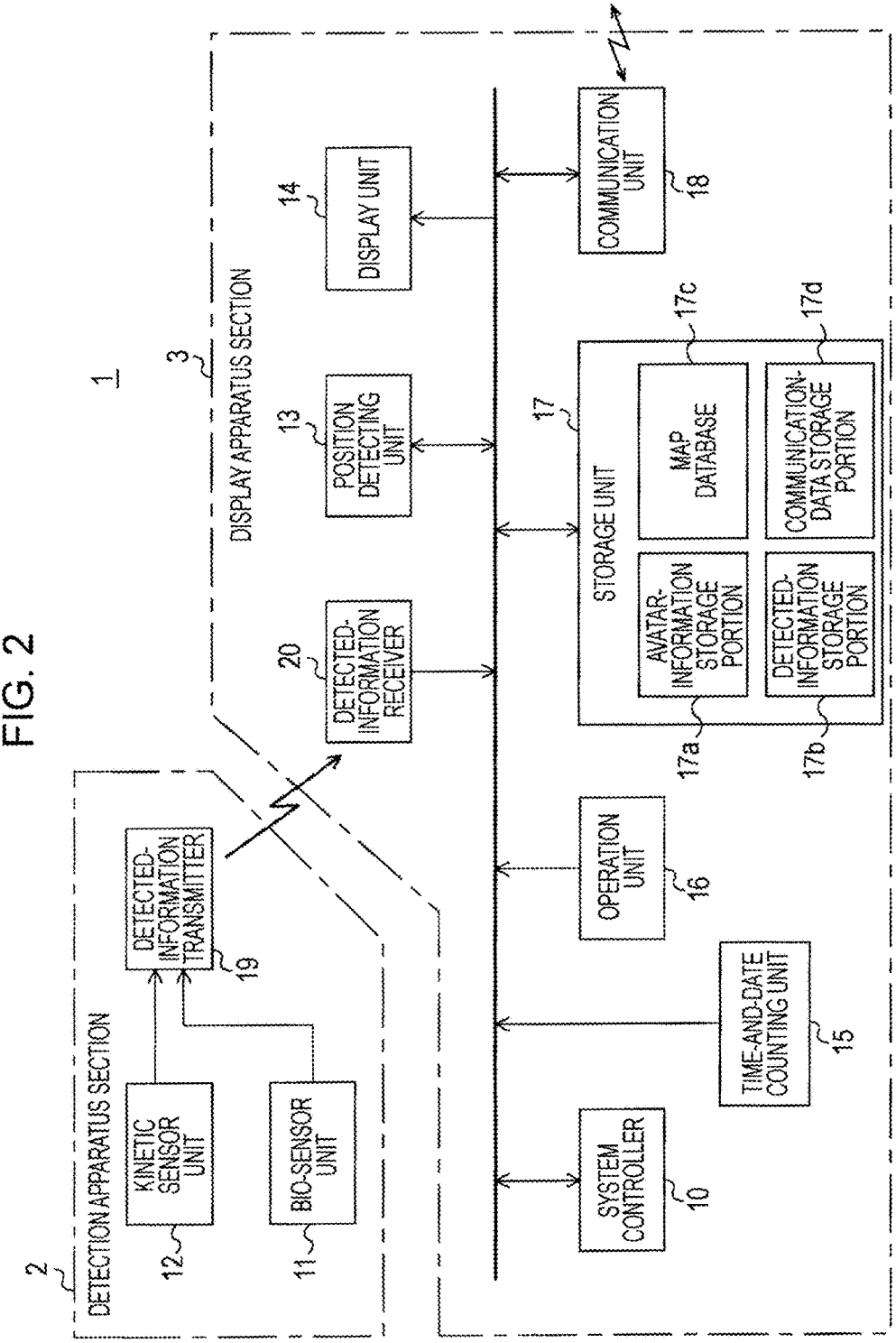
FIG. 2 is block diagram of another example of the information display apparatus according to the embodiment.

Since it is only necessary that at least the bio-sensor unit 11 (or the kinetic sensor unit 12 depending on the details of kinetic information to be detected) should be in contact with the user's body, the information display apparatus 1 may be constituted of two sections, as shown in FIG. 2.

FIG. 2 illustrates an example in which the information display apparatus 1 is constructed as two separate sections, namely, a detection apparatus section 2 and a display apparatus section 3.

The detection apparatus section 2 includes the bio-sensor unit 11, the kinetic sensor unit 12, and a detected-information transmitter 19.

The display apparatus section 3 includes, besides the system controller 10, the position detecting unit 13, the display unit 14, the time-and-date counting unit 15, the operation unit 16, the storage unit 17, and the communication unit 18, a detected-information receiver 20.

The detected-information receiver 20 and the detected-information transmitter 19 communicate with each other wirelessly or via cable. When wireless communication is performed, for example, a short distance wireless communication protocol, such as Bluetooth, may be employed. Alternatively, an optical communication protocol for performing data communication based on optical pulse modulation using visible light or invisible light may be employed. Alternatively, a long distance wireless communication protocol may be employed, or communication may be performed over a network.

In the example shown in FIG. 2, bio-information detected by the bio-sensor unit 11 and kinetic information detected by the kinetic sensor unit 12 are transmitted from the detected-information transmitter 19 and received at the detected-information receiver 20.

The system controller 10 performs an avatar display control operation based on the bio- and kinetic information received at the detected-information receiver 20.

In the exemplary structure shown in FIG. 2, since it is only necessary to make the detection apparatus section 2 come in contact with a necessary body portion such as the user's skin or head, the load on the user to wear the detection apparatus section 2 can be alleviated. In particular, since the detection apparatus section 2 has a simple structure including the bio-sensor unit 11, the kinetic sensor unit 12, and the detected-information transmitter 19, the size and weight of the detection apparatus section 2 can be easily reduced. Accordingly, the detection apparatus section 2 can be easily implemented as an apparatus that can be worn on or at a necessary body part.

The display apparatus section 3 may be implemented as a small dedicated apparatus carried by the user. Alternatively, for example, the display apparatus section 3 may be implemented by adding the function of the display apparatus section 3 to a portable apparatus, such as a cellular phone or a PDA. Alternatively, the display apparatus section 3 may not necessarily be carried or worn by the user. In that case, the display apparatus section 3 may be a relatively large apparatus. A desktop or notebook personal computer may execute the function of the display apparatus section 3.

1-2 Process of Displaying Avatar in Real-Time

Figure 5A:
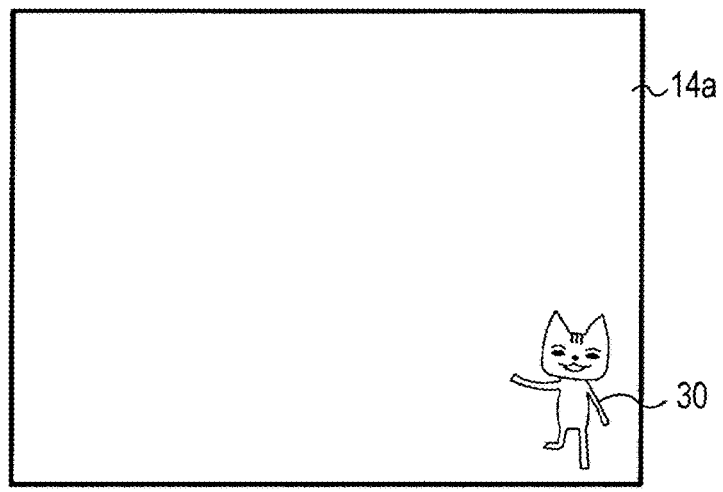
FIGS. 5A and 5B are illustrations of examples of displayed avatars according to the embodiment.
Figure 5B:
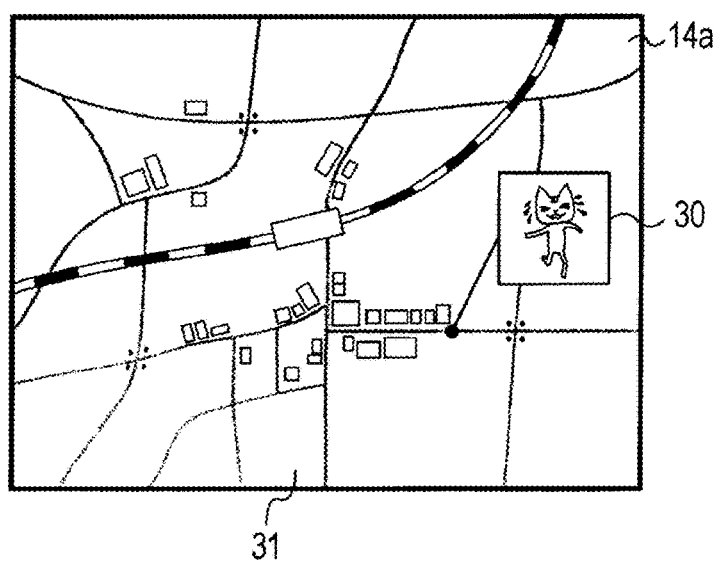

Referring to FIGS. 4, 5A, and 5B, a process of displaying an avatar using the information display apparatus 1 is described. The display process described below is an operation of constantly detecting bio- and kinetic information and displaying an avatar on the display unit 14 in accordance with the detected bio- and kinetic information, thereby representing a user's state in real-time.

For example, the information display apparatus 1 performs an operation of displaying on the display unit 14 a user's state in an avatar display mode started in response to an operation entered by the user.

FIG. 4 illustrates a control process performed by the system controller 10 for displaying an avatar in real-time.

When the avatar display mode starts, the system controller 10 advances the process from step F101 to step F102 and starts a process of displaying an avatar.

In step F102, the system controller 10 fetches bio- and kinetic information as information detected by the bio-sensor unit 11 and the kinetic sensor unit 12. Further, the system controller 10 fetches position information detected by the position detecting unit 13.

Next in step F103, the system controller 10 stores the fetched bio- and kinetic information and position information, together with the current time and date (seconds, minutes, hours, days, months, and years) counted by the time-and-date counting unit 15 at that time, in the detected-information storage portion 17b of the storage unit 17.

Next in step F104, the system controller 10 determines the user's state on the basis of the fetched bio- and kinetic information and decides which avatar to display.

The user's state may be a state represented by the bio- and kinetic information itself or may be a psychological or emotional state estimated from the bio- and kinetic information.

For example, whether the user's pulse is pounding can be determined from the heart rate or breathing information serving as bio-information.

Whether the user is still (standing or sitting), walking, or running can be determined from kinetic information.

The user's psychological state can be determined on the basis of bio-information. For example, the user's emotion (having fun, enjoying, or being happy, sad, afraid, calm, nostalgic, moved, surprised, excited, or stressed) can be estimated on the basis of a change in a numeral indicating bio-information due to a tense state, an excited state, or a comfortable state. This is because a detected value of the heart rate, pulse rate, brain wave, blood pressure, or GSR changes due to a psychological change. Further, the user's state (calm, irritated, etc) can be determined from the state of the pupils or the movement of the eyes detected by a vision sensor.

Further, the movement of the user's body detected by the kinetic sensor unit 12 may be used to determine the user's state. For example, when the user's pulse becomes fast, the user may be stressed or excited, or the user may be exercising, such as running. In order to determine the cause of the user's state, reference may be made to information obtained from an acceleration sensor or the like.

It takes a certain amount of time to estimate the psychological state. In some cases, the psychological state may not be accurately estimated simply by temporarily fetching information detected by the bio-sensor unit 11. That is, information detected by the bio-sensor unit 11, which serves as a signal obtained from a living body, changes its value every second. It is difficult to estimate the psychological state on the basis of the value obtained at a certain instance. In other cases, it is better to change a threshold for determining the physiological state in accordance with continuous changes in emotion.

It is thus appropriate to determine the physiological state by referring to continuous changes in bio- and kinetic information from a certain point in the past. For example, the processing in steps F102 to F109 in FIG. 4 is repeated during a period in the avatar display mode. With the processing in step F103, bio-information at each point is stored in the detected-information storage portion 17b. In step F104, the psychological state can be determined with reference not only to currently fetched bio-information, but also to items of stored bio-information from the past.

When the system controller 10 determines the user's state in, for example, the foregoing manner, the system controller 10 selects an avatar that matches the user's state. That is, avatars in accordance with the user's various states are stored in the avatar-information storage portion 17a of the storage unit 17, as shown in FIGS. 3A to 3F. The system controller 10 selects, from among these avatars, an avatar that matches the user's current state and decides that the selected avatar is an avatar to be displayed.

For example, when the user's current state is determined as a state in which the user is running and the pulse rate is greater than or equal to a certain threshold, the system controller 10 selects an avatar shown in FIG. 3E. The avatar shown in FIG. 3E represents that, using its expression and movement, the user is running and the pulse rate is high.

When the user's current state is determined as a state in which the user is still and depressed, the system controller 10 selects an avatar shown in FIG. 3F, which represents such a state using an expression and movement.

In step F105, the process is branched into two steps depending on whether the current mode is a map display mode. The map display mode is a state in which a map is displayed on the display unit 14 in response to a user operation. For example, when the user gives an instruction to select the avatar display mode while a map is being displayed or when the user gives an instruction to display a map image during the avatar display mode while the process shown in FIG. 4 is being performed, it is determined in step F105 that the current mode is the map display mode.

When the current mode is not the map display mode, the system controller 10 proceeds from step F105 to step F106 and performs an avatar display control operation. That is, the system controller 10 supplies the avatar data decided in step F104 to the display unit 14 and causes the display unit 14 to display the avatar based on the avatar data.

In contrast, when the current mode is the map display mode, the system controller 10 proceeds from step F105 to step F107 and, on the basis of the current position information, reads map image data in a range to be displayed from the map database 17c. In step F108, the system controller 10 generates display image data from the map image data and the avatar data, supplies the generated display image data to the display unit 14, and causes the display unit 14 to display the avatar on a map image. For example, the display unit 14 displays the avatar representing the user at a position corresponding to the current position on the map image.

The process returns to step F102 and similar processing is repeated until it is determined in step F109 that the avatar display mode is terminated.

For example, when the user enters a user operation to give an instruction to terminate the avatar display mode, the system controller 10 proceeds from step F109 to step F110 and terminates displaying the avatar on the display unit 14. Accordingly, the process shown in FIG. 4 is terminated.

FIGS. 5A and 5B illustrate examples of graphical representations.

FIG. 5A illustrates an example of a graphical representation displayed in response to the processing in step F106. In this case, an avatar 30 is displayed in the corner of a screen 14a of the display unit 14. For example, when a necessary image is displayed in the center of the screen 14a in a normal state, the avatar 30 is simply displayed in the corner of the screen 14a in a continuous manner. Alternatively, the avatar 30 may be enlarged and displayed in the center of the screen 14a.

Since the process shown in FIG. 4 is continuously performed during the avatar display mode, the displayed avatar 30 changes according to the user's state. For example, when the user starts running, an image shown in FIG. 3C is displayed. When the user continues running and has a faster pulse, the avatar 30 changes to an image shown in FIG. 3E.

FIG. 5B illustrates an example of a graphical representation displayed in response to the processing in step F108. A map image 31 is displayed on the screen 14a. In addition, the avatar 30 is displayed while the user's position (position based on position information detected by the position detecting unit 13) is indicated on the map. In this case, since the process shown in FIG. 4 is continuously performed, as the user's position moves or the user's state changes, the range of the displayed map image, the user's current position on the map, and the avatar 30 change as well.

By displaying an avatar in the foregoing manner, the user's state can be represented using an interesting image, which becomes more enjoyable to the user.

When the avatar is displayed together with the map image, the user's position and state can be clearly represented additionally using, for example, a navigation function.

Although the exemplary avatars in accordance with the user's various states are illustrated in FIGS. 3A to 3F, they are only examples in accordance with some of the user's states, and images representing the user's more versatile states can be prepared. For example, avatars having expressions and movements that represent various states, such as states in which the user feels hot or cold, the user is comfortable, tired, sleepy, or excited, the user has a low or high blood pressure, the user has raspy or easy breathing, or the user has a fast or slow heart rate, are prepared. It is only necessary to select one from among these avatars and display the selected avatar.

Avatars representing a certain user's state may be still images, moving images, or pseudo-moving images. Pseudo-moving images are in a display format in which a few (two or three) still images are alternately displayed.

Specific avatars may be prepared and stored in advance in the avatar-information storage portion 17a. Alternatively, for example, the communication unit 18 may communicate with an external server (e.g., the server apparatus 70 described later with reference to FIGS. 9 and 11) and download avatar data.

Alternatively, many basic avatars may be prepared and stored in advance, and a user may select one from among these basic avatars. Alternatively, a user may be allowed to create the user's own arbitrary avatar.

1-3 Process of Reproducing and Displaying Avatars as State History

By performing the processing in step F103 in FIG. 4, bio-information, kinetic information, and position information are sequentially stored in the detected-information storage portion 17b.

Even in a period outside the avatar display mode (period in which the process shown in FIG. 4 is not performed), when the system controller 10 performs the processing in steps F102 and F103 at, for example, constant time intervals, the user's bio-information, kinetic information, and position information are constantly stored in the detected-information storage portion 17b.

FIG. 6A illustrates an example of information stored in the detected-information storage portion 17b.

Referring to FIG. 6A, position information PL (PL1, PL2, PL3, . . . ), bio-information L (L1, L2, L3, . . . ), and kinetic information M (M1, M2, M3, . . . ) detected at corresponding times and dates are stored in association with corresponding items of time-and-date information.

For example, since detected items of bio-information, kinetic information, and position information are successively stored together with items of time-and-date information in the avatar-information storage portion 17a, the user's states in the past can be determined.

In step F104 of FIG. 4, the user's current state is determined, and which avatar to display is decided. Information indicating the selected avatar (or information on the user's state based on which the avatar is selected) may be stored as avatar-related information C (C1, C2, C3, . . . ) shown in FIG. 6B.

Further, avatar-related information C and position information PL may be stored in association with time-and-date information, but no bio-information or kinetic information may be stored, which is not shown in FIGS. 6A and 6B.

By storing these items of information, the information display apparatus 1 can reproduce and display avatars representing the user's states in the past.

FIG. 7 illustrates a process performed by the system controller 10 when reproducing and displaying avatars representing a user's state history.

When the user operates the operation unit 16 to give an instruction to reproduce an avatar, the system controller 10 proceeds from step F201 to step F202 and displays an image on the display unit 14 to prompt the user to enter a reproducing criterion.

A reproducing criterion, such as time and date, place, or the like, is a criterion used to search for stored data to reproduce. For example, when a time and date is used as a reproducing criterion, the user may be allowed to specify a specific date as X(month)/Y(day), a specific time and date as X(month)/Y(day), Z PM, or a specific range from A(month)/B(day) to X(month)/Y(day).

When a place is used as a reproducing criterion, the user may be allowed to specify the name of a place or to specify the range of a region on a map image.

Alternatively, the user may be allowed to specify bio-information, kinetic information, psychological state, or the like as a reproducing criterion. For example, the user may be allowed to specify that "the heart rate is greater than or equal to XX", "the user is running", or "the user is depressed".

The user may further add an AND operator or an OR operator to reproducing criteria, such as time and date, place, bio-information, kinetic information, and psychological state.

Alternatively, the user may specify to search for "all stored data".

The system controller 10 displays an image so that such a reproducing criterion described above can be entered and, in steps F203 and F204, waits for the user to enter a reproducing criterion.

When the user enters a reproducing cancel operation, the flow proceeds from step F204 to F209, and the system controller 10 stops displaying the image for prompting the user to enter a reproducing criterion. The process shown in FIG. 7 is terminated.

When the user enters a reproducing criterion, the flow proceeds from step F203 to step F205, and the system controller 10 extracts, from among items of data stored in the detected-information storage portion 17b, data matching the reproducing criterion and regards the extracted data as data to be reproduced.

For example, when a specific time and date is specified, a search based on the entered time and date is conducted through items of data stored as shown in FIG. 6A or 6B to extract data matching the entered time and date.

Having extracted the data to be reproduced, in step F206, the system controller 10 controls reproducing the extracted data.

Figure 8A:
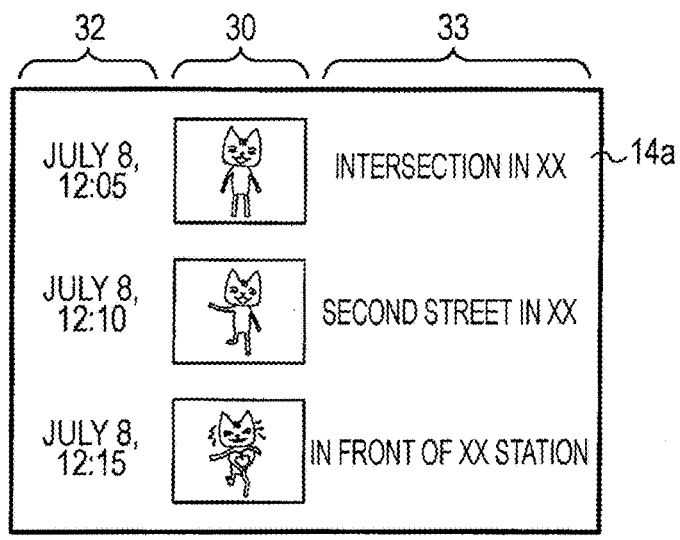
FIGS. 8A and 8B are illustrations of examples of reproduced and displayed avatars according to the embodiment.
Figure 8B:
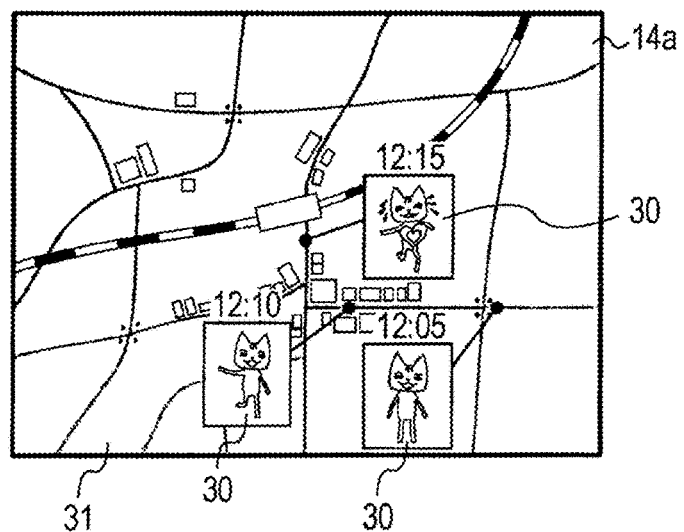

For example, FIGS. 8A and 8B show cases in which items of data shown in FIGS. 6A and 6B are reproduced and images represented by the reproduced items of data are displayed.

FIG. 8A shows an example in which a list of images represented by extracted items of data is displayed on the screen 14a of the display unit 14. In this exemplary case, a time-and-date indication 32 based on time-and-date information and a name-of-place indication 33 based on position information PL are displayed together with the avatar 30.

Alternatively, as shown in FIG. 8B, images represented by extracted items of data may be displayed on a map image. In this case, while a position based on position information PL is indicated on the map image 31, the corresponding avatar 30 and the time and date are displayed.

Other various display formats are conceivable.

When items of data are stored in the format shown in FIG. 6A, it is necessary to perform, for data determined to be reproduced, a process of determining the user's state on the basis of bio- and kinetic information and deciding which avatar to display (process similar to step F104 shown in FIG. 4). In contrast, when items of avatar-related information C are stored as shown in FIG. 6B, it is only necessary to display avatars represented by the avatar-related information C, as shown in FIGS. 8A and 8B.

In the graphical representations shown in FIGS. 8A and 8B, the displayed details are changed as the user scrolls on the screen or skips a page.

Alternatively, stored data to be reproduced may be automatically changed.

When the system controller 10 determines that reproducing is terminated in response to a user operation or a certain condition, the process proceeds from step F207 to step F208, and the system controller 10 terminates the reproducing and displaying process. The process shown in FIG. 7 is terminated.

For example, when avatars are reproduced and displayed on the basis of items of data stored in the detected-information storage portion 17b, the user can view the user's states or the places where the user has been at arbitrary points in the past. Accordingly, the user can easily remember and identify the places where the user has been and the user's states at those points in the past, which serve as the user's state history.

2. Displaying Avatar Based on Another Person's Bio- and Kinetic Information 2-1 System Configuration The foregoing description concerns the operation of the information display apparatus 1 which displays an avatar in accordance with the user's current state or which reproduces and displays avatars representing the user's past states. Hereinafter, an information processing system in which the user can be informed of another person's state using an avatar and apparatuses constituting the system are described.

FIG. 9 illustrates an example of a system configuration. This information processing system is an exemplary system in which transmitting apparatuses 100 (hereinafter may be collectively referred to as a "transmitting apparatus 100" when it is unnecessary to distinguish between the two), the server apparatus 70, and a display apparatus 200 can communicate with one another via the network 60.

In this system, a user of the display apparatus 200 can be informed of the state of another user wearing the transmitting apparatus 100 using an avatar.

The network 60 includes various types, such as the Internet, a mobile phone communication network, a personal handy phone (PHS) communication network, an ad-hoc network, and a local area network (LAN).

The transmitting apparatus 100 detects bio-information, kinetic information, position information, and time-and-date information of a person wearing the transmitting apparatus 100 and transmits the detected items of information to the server apparatus 70 by communicating via the network 60. For example, the transmitting apparatus 100 periodically transmits information.

The server apparatus 70 stores the transmitted bio-information, kinetic information, position information, and time-and-date information in an internal database. These items of information are stored in association with identification information (hereinafter referred to as a "user ID") uniquely given to the person wearing the transmitting apparatus 100, which will be described later.

The display apparatus 200 can obtain bio-information, kinetic information, position information, and time-and-date information of a specific user (another person), which are stored in the server apparatus 70, by communicating via the network 60. On the basis of the obtained items of information including bio- and kinetic information and the user ID, the display apparatus 200 decides which avatar to display and displays the avatar. When displaying the avatar, the display apparatus 200 may cause the avatar to reflect the position information and the time-and-date information.

Alternatively, the display apparatus 200 may obtain an avatar itself, which is to be displayed, from the server apparatus 70 by communicating via the network 60 and display the avatar.

The information display apparatus 1 with the structure shown in FIG. 1 may serve as the transmitting apparatus 100 or the display apparatus 200 shown in FIG. 9.

2-2 Structure of Transmitting Apparatus

Figure 10:
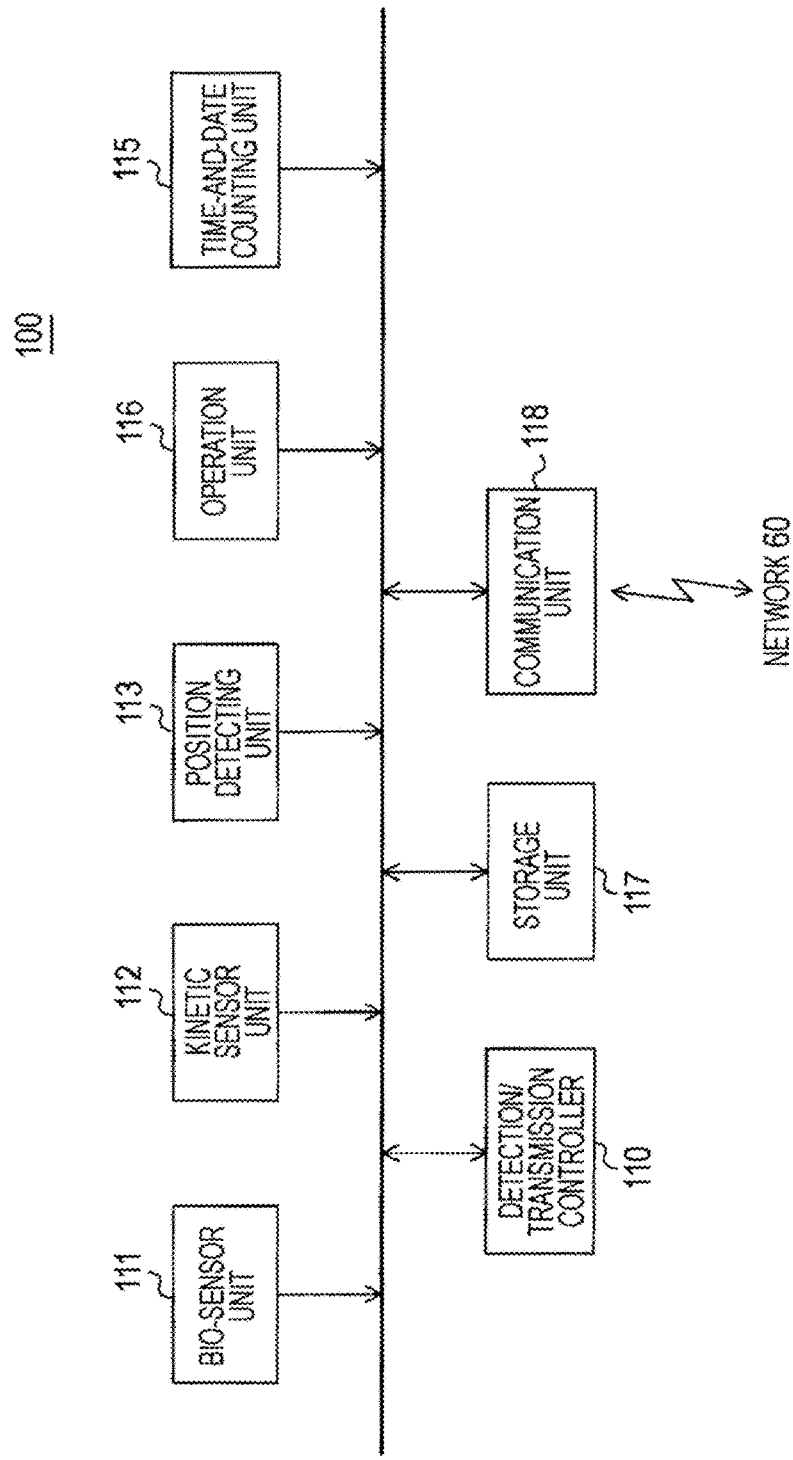
FIG. 10 is a block diagram of a transmitting apparatus according to the embodiment.

FIG. 10 shows an exemplary structure of the transmitting apparatus 100 shown in FIG. 9.

The transmitting apparatus 100 includes a detection/transmission controller 110, a bio-sensor unit 111, a kinetic sensor unit 112, a position detecting unit 113, a time-and-date counting unit 115, an operation unit 116, a storage unit 117, and a communication unit 118.

The detection/transmission controller 110 is implemented by, for example, a CPU. The detection/transmission controller 110 performs a control process for detecting and transmitting bio-information.

The storage unit 117 has storage areas including a ROM, a RAM, and a non-volatile memory and is used as a storage area for a processing program executed by the detection/transmission controller 110 and a work area. Alternatively, the storage unit 117 may be implemented by an internal memory of a microchip computer serving as the detection/transmission controller 110.

The non-volatile memory area in the storage unit 117 may store identification information (apparatus ID) uniquely given to each of the transmitting apparatuses 100 and identification information (user ID) of the user of each of the transmitting apparatuses 100.

The communication unit 118 performs data transmission/reception with an external apparatus. In particular, in the case of the system configuration shown in FIG. 9, the communication unit 118 performs data communication with the server apparatus 70 as communication via the network 60. In this case, the communication unit 118 is only necessary to be connected to the network 60 via cable or wirelessly and to perform communication. For example, the communication unit 118 may perform wireless communication with a network access point.

The operation unit 116 is provided for the user to enter operations necessary for using the transmitting apparatus 100. Using the operation unit 116, the user may enter, for example, power on/off operations and various setting operations.

The bio-sensor unit 111, the kinetic sensor unit 112, the position detecting unit 113, and the time-and-date counting unit 115 have functions similar to those of the bio-sensor unit 11, the kinetic sensor unit 12, the position detecting unit 13, and the time-and-date counting unit 15 of the information display apparatus 1 illustrated in FIG. 1. With these units, the user's bio-information, kinetic information, position information, and time-and-date information are detected.

In the transmitting apparatus 100 described above, the detection/transmission controller 110 periodically stores, for example, the user's bio-information, kinetic information, position information, and time-and-date information at a detection point, which are detected by the bio-sensor unit 111, the kinetic sensor unit 112, the position detecting unit 113, and the time-and-date counting unit 115, respectively, in the storage unit 117. Using the bio-information, kinetic information, position information, and time-and-date information fetched into the storage unit 117, the detection/transmission controller 110 generates transmission data and causes the communication unit 118 to transmit the transmission data to the server apparatus 70 via the network 60. In this case, the transmission data includes, besides the bio-information, kinetic information, position information, and time-and-date information, the user ID or the apparatus ID.

It is preferable that the transmitting apparatus 100 described above be constructed as a small and light-weight apparatus so that the user can easily wear the apparatus. Depending on the details of bio- and kinetic information to be detected, it is preferable that the transmitting apparatus 100 be constructed as, for example, a wrist watch type, glasses type, headset type, hat type, helmet type, or glove type apparatus or as clothing including the apparatus. In particular, the transmitting apparatus 100 is preferably constructed so that a part (the bio-sensor unit 111) of the transmitting apparatus 100 can be in contact with an appropriate body part, such as the skin or head of a subject, in accordance with details of information to be detected.

Alternatively, as in the example shown in FIG. 2, the bio-sensor unit 111 and the kinetic sensor unit 112 may be constructed as independent units, which are not shown in a drawing.

As is clear from the comparison of the structure shown in FIG. 10 with the structures shown in FIGS. 1 and 2, the information display apparatus 1 illustrated in FIGS. 1 and 2 may perform the same operation as the transmitting apparatus 100 shown in FIG. 10 and function as the transmitting apparatus 100 shown in FIG. 9. That is, for example, the system controller 10 shown in FIG. 1 may periodically generate transmission data using bio-information, kinetic information, position information, and time-and-date information and cause the communication unit 18 to transmit the transmission data to the server apparatus 70 via the network 60.

2-3 Structure of Server Apparatus

Figure 11:
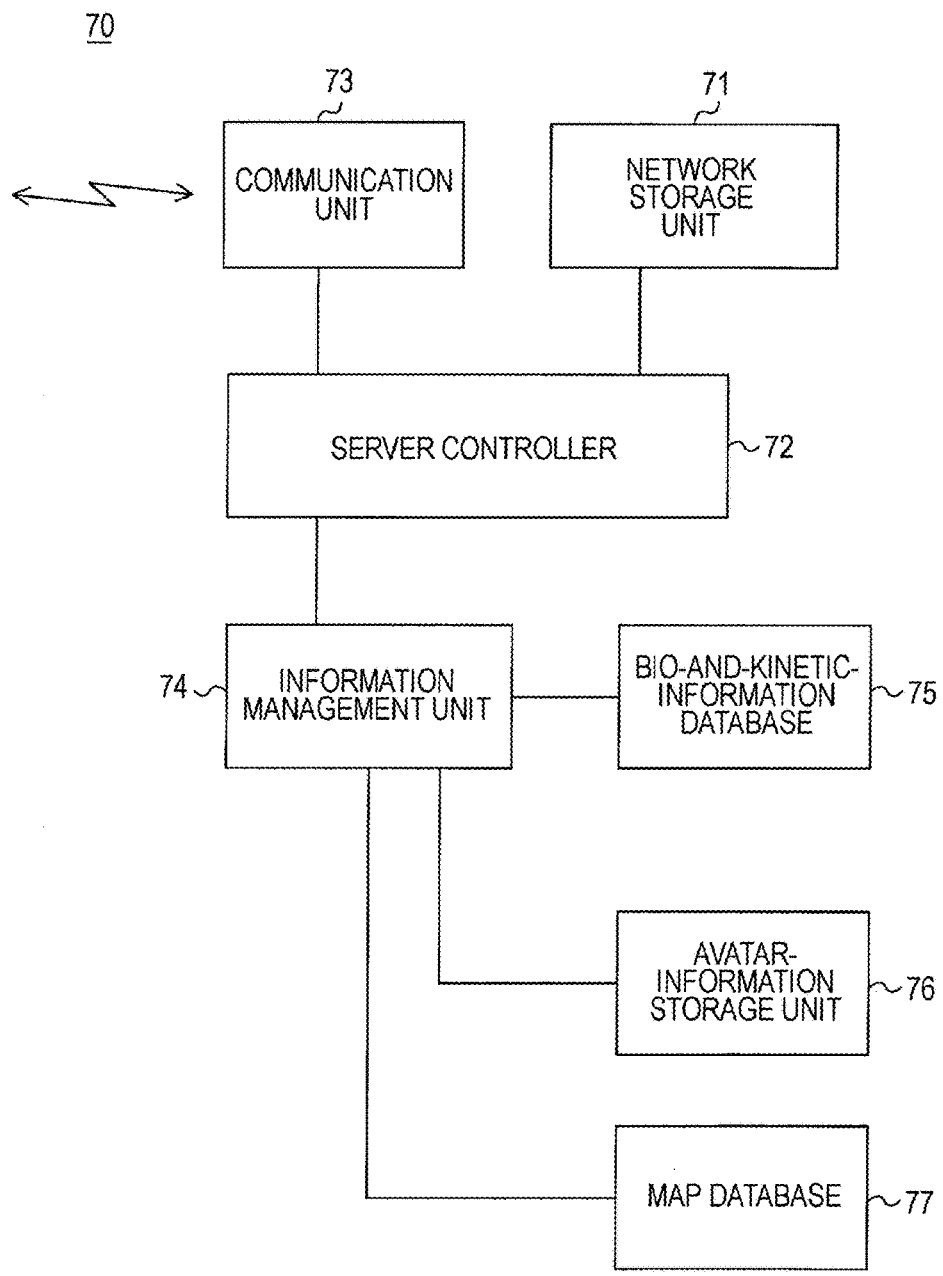
FIG. 11 is a block diagram of a server apparatus according to the embodiment.

FIG. 11 shows an exemplary structure of the server apparatus 70.

As has been described above, the server apparatus 70 is an apparatus that can store, for example, bio-information, kinetic information, position information, and time-and-date information transmitted from the transmitting apparatus 100 by communicating via the network 60 and transmit the stored items of information to the display apparatus 200.

The server apparatus 70 includes a server controller 72, a network storage unit 71, a communication unit 73, an information management unit 74, and a bio-and-kineticinformation database 75. The server apparatus 70 may further include an avatar-information storage unit 76 and a map database 77.

The server controller 72 performs operation control necessary as the server apparatus 70. In particular, the server controller 72 controls the network communication operation, processes performed upon receipt of bio-information, kinetic information, position information, and time-and-date information transmitted from the transmitting apparatus 100, and transmission of these items of information to the display apparatus 200.

The network storage unit 71 is implemented by, for example, an HDD. For example, the network storage unit 71 temporarily stores transmission/reception data communicated between the transmitting apparatus 100 and the display apparatus 200 via the network 60 and stores various items of necessary data.

The communication unit 73 performs data communication via the network 60 with the transmitting apparatus 100 and the display apparatus 200.

The information management unit 74 manages the bio-information, kinetic information, position information, and time-and-date information transmitted from the transmitting apparatus 100.

The bio-and-kinetic-information database 75 stores the bio-information, kinetic information, position information, and time-and-date information transmitted from the transmitting apparatus 100 in association with, for example, the user ID in the bio-and-kinetic-information database 75.

In addition, the information management unit 74 registers data into the bio-and-kinetic-information database 75 and searches for data in the bio-and-kinetic-information database 75.

The avatar-information storage unit 76 stores various avatars to be displayed using the display apparatus 200. In particular, the avatar-information storage unit 76 may store avatars so that each avatar is managed in association with a user ID.

The map database 77 stores map images for displaying maps using the display apparatus 200 and other necessary data.

2-4 Structure of Display Apparatus

Figure 12:
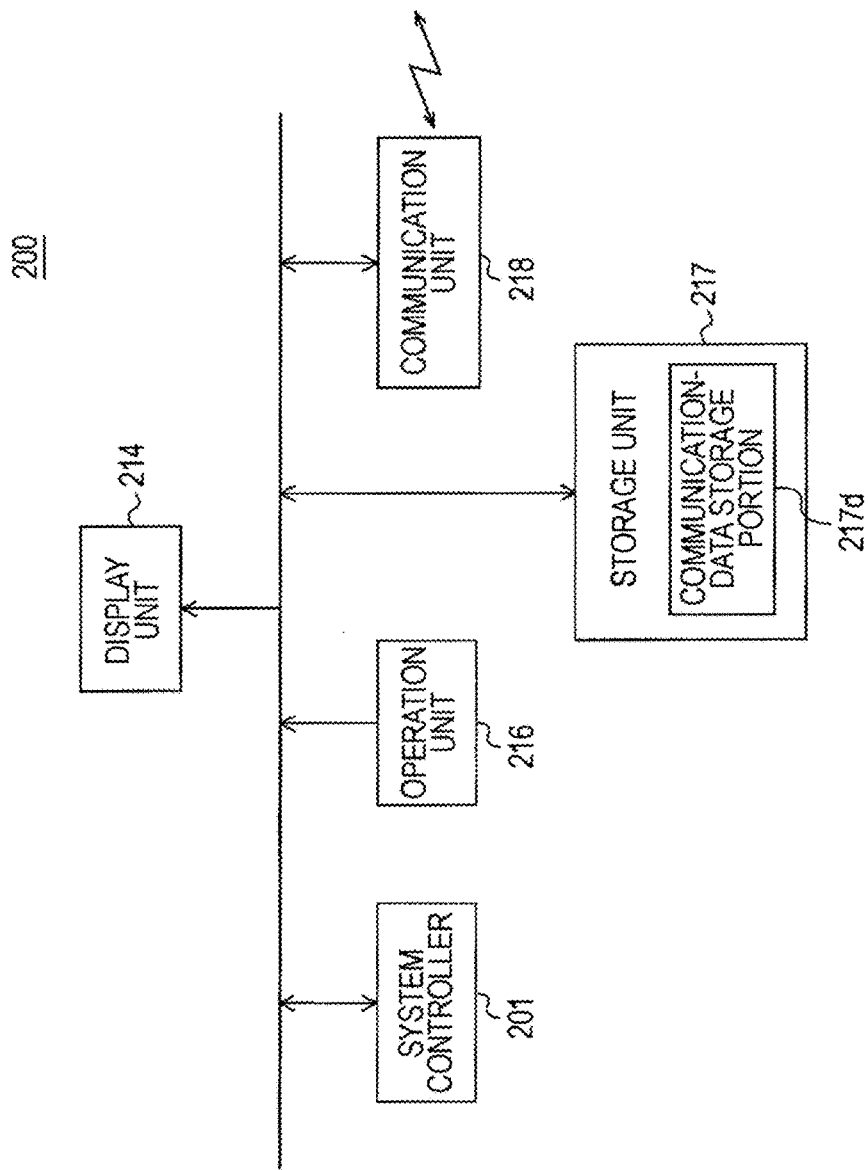
FIG. 12 is a block diagram of a display apparatus according to the embodiment.
Figure 13:
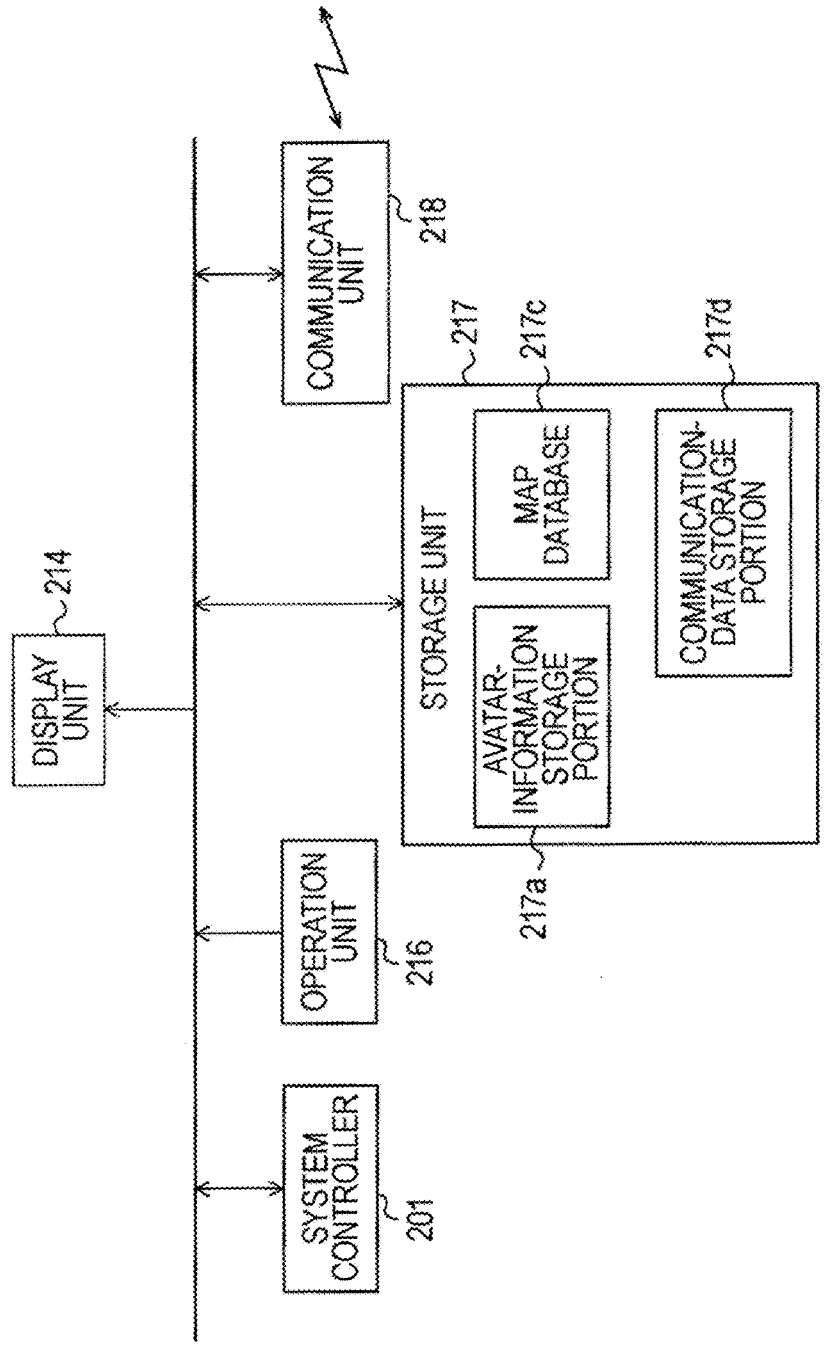
FIG. 13 is a block diagram of another example of the display apparatus according to the embodiment.

Referring now to FIGS. 12 and 13, examples of the structure of the display apparatus 200 will be described.

The display apparatus 200 shown in FIG. 12 includes a system controller 201, a communication unit 218, a display unit 214, an operation unit 216, and a storage unit 217. A storage area serving as a communication-data storage portion 217*d* is provided in the storage unit 217.

The example of the structure of the display apparatus 200 shown in FIG. 13 includes, in addition to the structure shown in FIG. 12, storage areas serving as an avatar-information storage portion 217*a* and a map database 217*c* provided in the storage unit 217.

Since these units of the structure shown in each of FIGS. 12 and 13 are similar to the system controller 10, the communication unit 18, the display unit 14, the operation unit 16, and the storage unit 17 shown in FIG. 1, descriptions thereof are not repeated to avoid redundancy.

In particular, the communication unit 218 performs data communication with the server apparatus 70 as communication via the network 60 shown in FIG. 9.

The system controller 201 controls an avatar display operation and a process of communicating with the server apparatus 70.

The display apparatus 200 illustrated in the system configuration shown in FIG. 9 is only necessary to display, on the display unit 214, an avatar representing the state of a certain person (the user of the transmitting apparatus 100, who is a stranger to the user of the display apparatus 200) on the basis of information received from the server apparatus 70.

Accordingly, two types of the structure of the display apparatus 200 are conceivable in view of the system operation.

An avatar in this example is an image representing a user's state determined on the basis of bio- and kinetic information.

That is, which avatar to display is decided on the basis of the user's state determined from bio- and kinetic information. In view of the system operation, a process of deciding which avatar to display may be performed using the server apparatus 70 or the display apparatus 200.

When the server apparatus 70 decides which avatar to display on the basis of the user's state determined from bio- and kinetic information, the server apparatus 70 can transmit avatar data itself to the display apparatus 200. In this case, the display apparatus 200 stores the received avatar data in the communication-data storage portion 217*d* and thereafter displays the avatar using the avatar data. Accordingly, the display apparatus 200 can be realized as the structure shown in FIG. 12.

Alternatively, when the server apparatus 70 decides which avatar to display on the basis of the user's state determined from bio- and kinetic information, the server apparatus 70 may transmit, instead of avatar data itself, information for specifying an avatar to be displayed or information for specifying the expression or movement of an avatar to be displayed to the display apparatus 200.

In this case, the display apparatus 200 selects an avatar on the basis of the received information and displays the avatar. Accordingly, it is preferable for the display apparatus 200 to have the structure shown in FIG. 13, which includes the avatar-information storage portion 217*a*.

When displaying a map image, in the case where the display apparatus 200 downloads map image data from the server apparatus 70, the display apparatus 200 stores the downloaded map data in the communication-data storage portion 217*d* and thereafter displays the map image using the map data. Accordingly, the display apparatus 200 can have the structure shown in FIG. 12, which has no map database.

In contrast, when the system operation involves the display apparatus 200 performing a process of deciding which avatar to display, the structure shown in FIG. 13 is appropriate.

In this case, the server apparatus 70 at least transmits a certain person's (user ID) bio- and kinetic information to the display apparatus 200, and the display apparatus 200 decides which avatar to display on the basis of the user's state determined from the received bio- and kinetic information and displays the avatar. Accordingly, the server apparatus 70 is necessary to have the avatar-information storage portion 217*a*.

As is clear from the foregoing description, the structure shown in FIG. 12 corresponds to the case which assumes the system operation in which the server apparatus 70 transmits avatar data and which intends to simplify the display apparatus 200. In contrast, the structure shown in FIG. 13 is the exemplary structure that can be used regardless of which of the server apparatus 70 and the display apparatus 200 performs the avatar deciding process.

Similarly, the information display apparatus 1 shown in FIG. 1 may function as the display apparatus 200 regardless of which of the server apparatus 70 and the information display apparatus 1 performs the avatar deciding process.

2-5 System Operation for Displaying Avatar

An exemplary operation of the information processing system including the transmitting apparatus 100, the server apparatus 70, and the display apparatus 200 is described.

Figure 14:
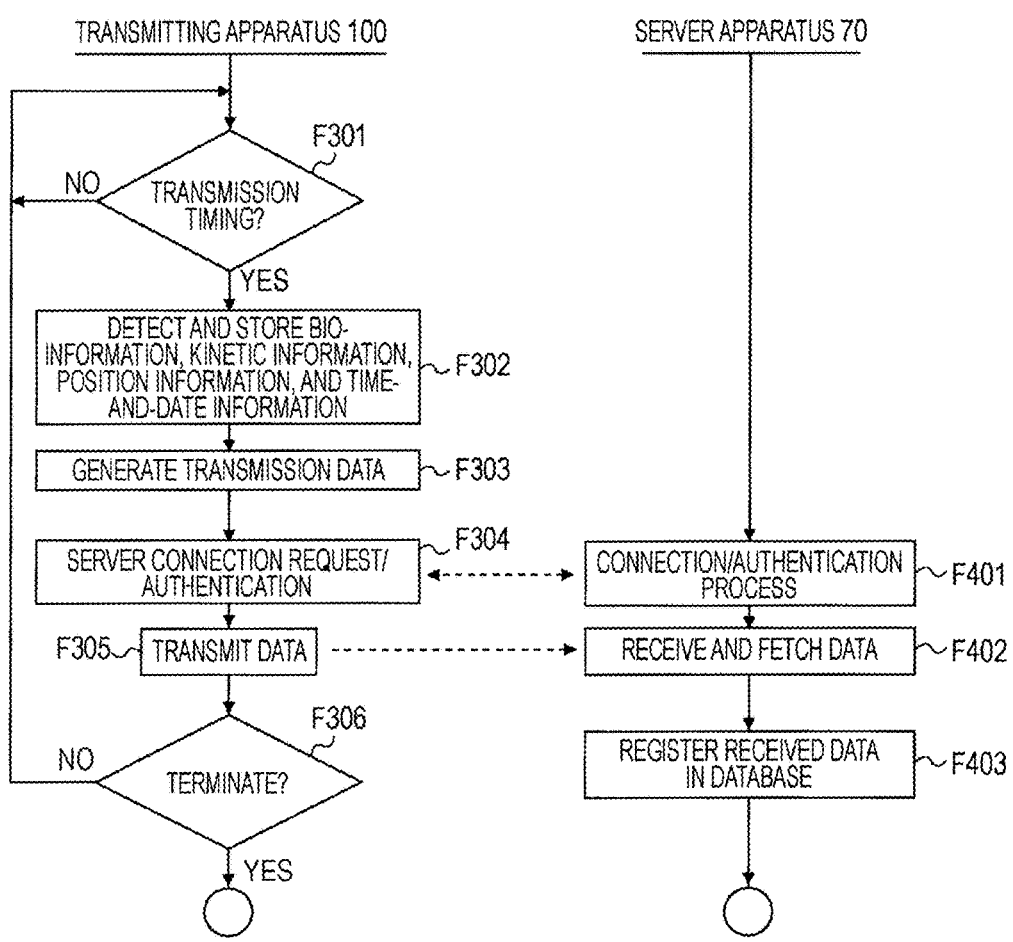
FIG. 14 is a flowchart of a process of transmitting bio-information and the like to the server apparatus according to the embodiment.

FIG. 14 illustrates the operation of transmitting bio-information and the like from the transmitting apparatus 100 to the server apparatus 70. Referring to FIG. 14, a process performed by the transmitting apparatus 100 is a process executed under control of the detection/transmission controller 110, and a process performed by the server apparatus 70 is a process executed under control of the server controller 72.

In the transmitting apparatus 100, the detection/transmission controller 110 waits for a transmission timing in step F301. When the transmission timing has come, the flow proceeds to step F302. The transmission timing may be, for example, a periodical timing or a timing based on a user operation or any other trigger.

In step F302, the detection/transmission controller 110 fetches bio-information obtained by the bio-sensor unit 111, kinetic information obtained by the kinetic sensor unit 112, position information obtained by the position detecting unit 113, and the current time-and-date information obtained by the time-and-date counting unit 115 and stores these items of information in the storage unit 117.

In step F303, the detection/transmission controller 110 generates transmission data. That is, the detection/transmission controller 110 generates transmission data including the bio-information, kinetic information, position-information, and time-and-date information fetched into the storage unit 117, and the user ID or the apparatus ID.

In step F304, the transmitting apparatus 100 establishes a communication connection with the server apparatus 70. The detection/transmission controller 110 causes the communication unit 118 to start communicating via the network 60 to establish a communication connection with the server apparatus 70. In this case, in step F401, the server controller 72 of the server apparatus 70 causes the communication unit 73 to perform a communication connection process and performs an authentication process. The authentication process can be performed using various methods. For example, in one method, the transmitting apparatus 100 transmits its apparatus ID to the server apparatus 70, and the server apparatus 70 determines whether this apparatus ID is an appropriately registered apparatus ID.

When the authentication is successful and a connection is established, the transmitting apparatus 100 transmits data. That is, the detection/transmission controller 110 causes the communication unit 118 to transmit data including bio-information, kinetic information, position information, time-and-date information, and user ID (or apparatus ID).

In contrast, the server controller 72 of the server apparatus 70 fetches, in step F402, the data received at the communication unit 73 into the network storage unit 71.

When the reception data is completely fetched, in step F403, the server controller 72 decodes the fetched reception data and extracts data from the decoded data. The server controller 72 transfers bio-information, kinetic information, position information, time-and-date information, and user ID (or apparatus ID) included in the reception data to the information management unit 74 and registers these items of data in the bio-and-kinetic-information database 75.

Until the operation is terminated (such as by turning off the power), the transmitting apparatus 100 returns from step F306 to step F301 and, for example, every time the periodical transmission timing has come, performs the processing in steps F302 to F305 described above.

For example, when the foregoing process is performed in a sequential manner, the bio-and-kinetic-information database 75 of the server apparatus 70 stores information transmitted from the transmitting apparatus 100.

FIG. 15 illustrates an example of a registration format of the bio-and-kinetic-information database 75.

In the bio-and-kinetic-information database 75, for example, bio-information L, kinetic information M, position information PL, and time-and-date information Date are stored in association with the user ID (UID 1, UID 2, . . . ).

For example, every time bio-information L, kinetic information M, position information PL, and time-and-date information Date are transmitted, together with the user ID (UID 1), from the transmitting apparatus 100 worn by the user whose user ID is UID 1 by performing the process shown in FIG. 14, the bio-information L, kinetic information M, position information PL, and time-and-date information Date are additionally stored in association with the user ID (UID 1), as shown in FIG. 15, as items of data in one registration unit.

Regarding the stored data, the number of registration units stored for each user ID may be limited, and older data may be deleted one after another. Alternatively, older data may be deleted with reference to the time-and-date information.

Alternatively, data (L, M, PL, and Date) in only one registration unit may be stored for each user ID. That is, the storage format may be such that, every time bio-information L, kinetic information M, position information PL, and time-and-date information Date for a certain user ID are transmitted, the bio-information L, kinetic information M, position information PL, and time-and-date information Date for that user ID are updated.

Alternatively, a database registering bio-information and the like using, instead of the user ID (or together with the user ID), the apparatus ID may be employed.

On the basis of these items of information stored in the server apparatus 70 in this manner, the display apparatus 200 can display an avatar representing the state of a person who is a stranger to the user of the display apparatus 200.

Figure 16:
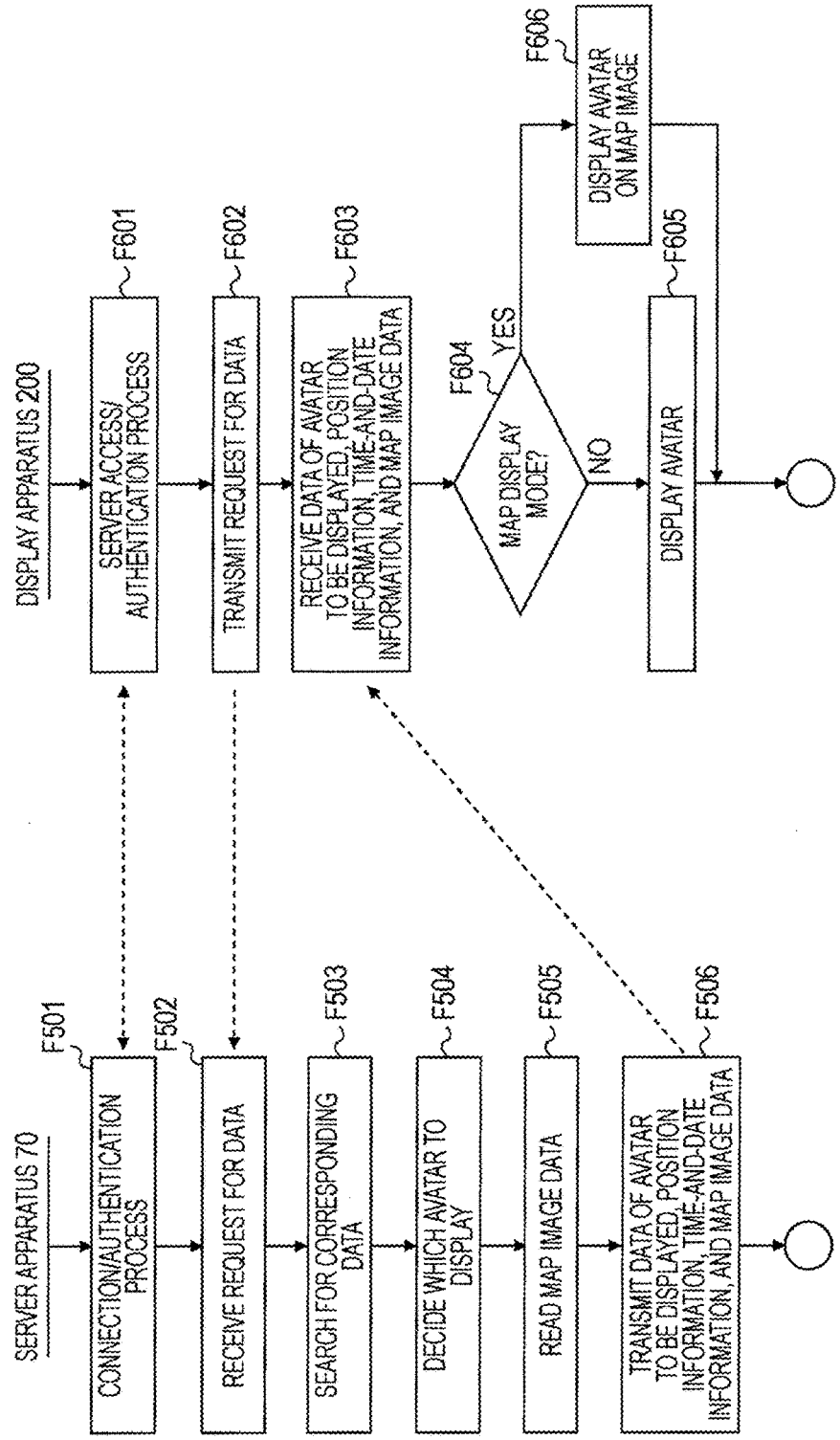
FIG. 16 is a flowchart of a process of transmitting data to the display apparatus and displaying an image represented by the data according to the embodiment.
Figure 17:
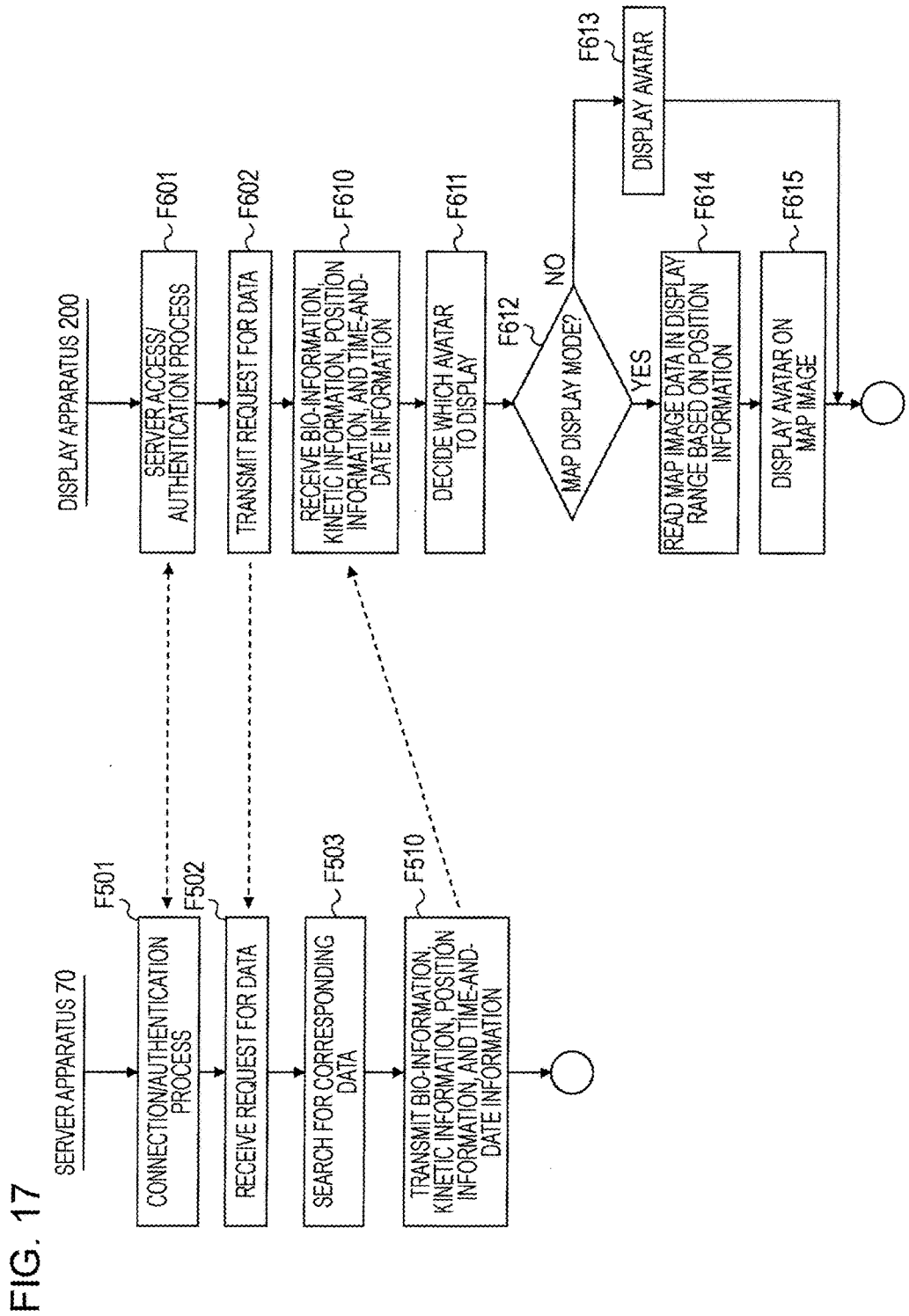
FIG. 17 is a flowchart of another example of the process of transmitting data to the display apparatus and displaying an image represented by the data according to the embodiment.

Examples of processes for performing the foregoing operations are illustrates in FIGS. 16 and 17.

FIGS. 16 and 17 illustrate processes performed by the server apparatus 70 and the display apparatus 200. A process performed by the server apparatus 70 is a process under control of the server controller 72. A process performed by the display apparatus 200 is a process under control of the system controller 201.

FIG. 16 illustrates an exemplary process performed in the case where the server apparatus 70 decides on an avatar. FIG. 17 illustrates another exemplary process performed in the case where the display apparatus 200 decides on an avatar.

The exemplary process shown in FIG. 16 is described.

When the user of the display apparatus 200 wants to be informed of the current state of another person (such as a friend), the user enters an operation to specify that other person's user ID (or apparatus ID) and instructs the display apparatus 200 to access the server apparatus 70. For example, when the user knows the other person's user ID, the user can enter an operation to request for a graphical representation of the other person's state by specifying the other person's user ID.

In response to such a user operation, the display apparatus 200 performs a process shown in FIG. 16 in order to display an avatar representing the other person's state.

In step F601, the display apparatus 200 establishes a communication connection with the server apparatus 70. The system controller 201 causes the communication unit 218 to start communicating via the network 60 to establish a communication connection with the server apparatus 70. In this case, in step F501, the server controller 72 of the server apparatus 70 causes the communication unit 73 to perform a communication connection process and performs an authentication process. Also in this case, the authentication process can be performed using various methods. For example, in one method, the display apparatus 200 transmits the user ID of the user thereof or the apparatus ID thereof to the server apparatus 70, and the server apparatus 70 checks the user ID or the apparatus ID.

When the authentication of communication with the server apparatus 70 is successful and a connection with the server apparatus 70 is established, the system controller 201 of the display apparatus 200 transmits, in step F602, a request for data, which includes the other person's user ID (or apparatus ID) specified by the user of the display apparatus 200, to the server apparatus 70.

Upon detection of receipt of the request for the data in step F502, the server controller 72 transfers in step F503 the user ID (or apparatus ID) to the information management unit 74 and gives an instruction to search for the corresponding data. The information management unit 74 extracts, from the bio-and-kinetic-information database 75, data (including bio-information L, kinetic information M, position information PL, and time-and-date information Date) corresponding to the specified user ID (or apparatus ID). In this case, when bio-information L, kinetic information M, position information PL, and time-and-date information Date constitute one registration data unit and when multiple registration data units are stored, bio-information L, kinetic information M, position information PL, and time-and-date information Date serving as the most recent registration data unit may be read on the basis of the time-and-date information Date.

Next in step F504, the server controller 72 causes the information management unit 74 to perform a process of deciding which avatar to display.

On the basis of the read bio-information L, kinetic information M, position information PL, and time-and-date information Date, the information management unit 74 determines the user's state particularly using the bio-information L and the kinetic information M. From among various avatars stored in the avatar-information storage unit 76, the information management unit 74 decides on an avatar with an expression or movement in accordance with the determined user's state.

In this case, when different avatars are prepared for different user IDs, the user ID is additionally used to decide which avatar to display.

In step F505, the server controller 72 instructs the information management unit 74 to read map image data. On the basis of position information PL read from the bio-and-kinetic-information database 75, the information management unit 74 reads, from the map database 77, map image data within a necessary range including a position indicated by the position information PL.

In step F506, the server controller 72 receives, from the information management unit 74, data of the decided avatar to be displayed (e.g., avatar data itself), the position information PL, the map image data, and the time-and-date information Date and causes the communication unit 73 to transmit these items of information to the display apparatus 200.

The data of the avatar appropriately includes, when the display apparatus 200 has the structure shown in FIG. 12, the avatar data itself. However, when the display apparatus 200 stores avatars as in the structure shown in FIG. 13 or FIG. 1, the data of the avatar may include information for specifying the avatar or information for determining the user's state in order to specify the avatar.

In step F603, the system controller 201 of the display apparatus 200 receives the data of the avatar, the map image data, the position information PL, and the time-and-date information Date. That is, these items of data received at the communication unit 218 are stored in the communication-data storage portion 217*d* of the storage unit 217.

On the basis of the received and saved data, the avatar is displayed.

In this case, the system controller 201 determines, in step F604, whether the current mode is the map display mode. This is similar to the processing in step F105 of FIG. 4.

When the current mode is not the map display mode, in step F605, the system controller 201 causes the display unit 214 to display the avatar. That is, the system controller 201 supplies the received and saved avatar data to the display unit 214 and causes the display unit 214 to display the avatar illustrated in, for example, FIG. 5A.

In contrast, when the current mode is the map display mode, in step F606, the system controller 201 causes the display unit 214 to display the avatar on a map image. That is, the system controller 201 supplies the received and saved avatar data and map image data to the display unit 214 and causes the display unit 214 to display the avatar and the map illustrated in, for example, FIG. 5B.

In this case, from the avatar, the user of the display apparatus 200 can be informed of the current state (state based on the most recent bio- and kinetic information stored in the server apparatus 70) of the other person (friend).

FIG. 17 illustrates an exemplary process performed in the case where the display apparatus 200 decides which avatar to display. Steps in FIG. 17 which are the same as those in FIG. 16 are given the same step numerals.

Steps F601 and F602 of the display apparatus 200 and steps F501 and F502 of the server apparatus 70 are the same as those shown in FIG. 16. With the processing in these steps, communication is established, and a request for data is transmitted and received.

Upon detection of receipt of the request for the data in step F502, the server controller 72 transfers in step F503 the user ID (or apparatus ID) to the information management unit 74 and gives an instruction to search for the corresponding data. In response to this, as in FIG. 16, the information management unit 74 extracts, from the bio-and-kinetic-information database 75, data (including bio-information L, kinetic information M, position information PL, and time-and-date information Date) corresponding to the specified user ID (or apparatus ID).

In step F510, the server controller 72 receives the bio-information L, kinetic information M, position information PL, and time-and-date information Date read by the information management unit 74 and causes the communication unit 73 to transmit these items of information to the display apparatus 200.

In step F610, the system controller 201 of the display apparatus 200 receives the bio-information L, kinetic information M, position information PL, and time-and-date information Date. That is, these items of data received at the communication unit 218 are stored in the communication-data storage portion 217*d* of the storage unit 217.

Next in step F611, the system controller 201 performs a process of deciding which avatar to display. That is, using the received bio-information L and kinetic information M, the system controller 201 determines the other person's user state. From among various avatars stored in the avatar-information storage portion 17*a*, the system controller 201 decides on an avatar with an expression or movement in accordance with the determined user's state.

In this case, when different avatars are prepared for different user IDs, the other person's user ID specified at the time access is gained to the server apparatus 70 is additionally used to decide which avatar to display.

When which avatar to display is decided, the avatar is displayed.

In this case, the system controller 201 determines, in step F612, whether the current mode is the map display mode. This is similar to the processing in step F105 of FIG. 4.

When the current mode is not the map display mode, in step F613, the system controller 201 causes the display unit 214 to display the avatar. That is, the system controller 201 supplies data of the decided avatar to the display unit 214 and causes the display unit 214 to display the avatar illustrated in, for example, FIG. 5A.

In contrast, when the current mode is the map display mode, in step F614, the system controller 10 reads from the map database 17*c* map image data within a range to be displayed on the basis of the received position information PL and causes the display unit 214 to display the avatar on a map image. That is, the system controller 201 supplies the avatar data and the map image data to the display unit 214 and causes the display unit 214 to display the avatar and the map image illustrated in, for example, FIG. 5B.

In this case, from the avatar, the user of the display apparatus 200 can be informed of the current state (state based on the most recent bio- and kinetic information stored in the server apparatus 70) of the other person (friend).

When the foregoing system operation is performed, the user of the display apparatus 200 can be informed, from a displayed avatar, the current state of another person who is wearing the transmitting apparatus 100. For example, the user of the display apparatus 200 can check, from avatars, various states of a friend, such as states in which the friend is running, depressed, and the like.

In the foregoing description, the current state of another person is displayed using an avatar. Alternatively, the past state of another person may be displayed.

For example, in the case where bio-information and the like of the user of the transmitting apparatus 100 are stored in the bio-and-kinetic-information database 75 of the server apparatus 70 for a certain period of time, when a point in the past within this information storage range is specified and when this other person's bio-information and the like can be extracted from the stored information, the past state of this other person can be displayed using an avatar.

In this example, the user of the display apparatus 200 is informed of the state of another person, such as a friend, provided that the user of the display apparatus 200 knows the user ID of this other person. Alternatively, the user of the display apparatus 200 may be informed of the state of a complete stranger or a celebrity using a displayed avatar. For example, when a certain person authorizes to make his or her own state public and registers in the system, the user of the display apparatus 200 can arbitrary display the state of this person who has authorized to make his or her own state public.

3. Displaying Avatars Based on User's and Another Person's Bio- and Kinetic Information The foregoing description concerns the example in which the information display apparatus 1 displays an avatar representing the state of the user of the information display apparatus 1 and the example in which the display apparatus 200 displays an avatar representing another person's state. Alternatively, both the user's state and another person's state can be simultaneously displayed using avatars.

For example, in the system configuration shown in FIG. 9, it is assumed that the display apparatus 200 has the structure serving as the information display apparatus 1 shown in FIG. 1.

The information display apparatus 1 may perform the process shown in FIG. 4 in order to display an avatar representing the state of the user of the information display apparatus 1. In order to display an avatar representing another user's state, the information display apparatus 1 may perform the operation described as the process performed by the display apparatus 200 in FIG. 16 or 17.

That is, in the structure shown in FIG. 1, when the system controller 10 performs in parallel the process shown in FIG. 4 and the process shown in FIG. 16 or 17, the display unit 14 can display avatars representing the user and the other person.

For example, two avatars may be displayed on a screen. Alternatively, referring to FIG. 18, the user's state and another person's state may be represented using avatars 30A and 30B, respectively, while the positions of the user and the other person may be indicated on the map image 31.

Figure 18:
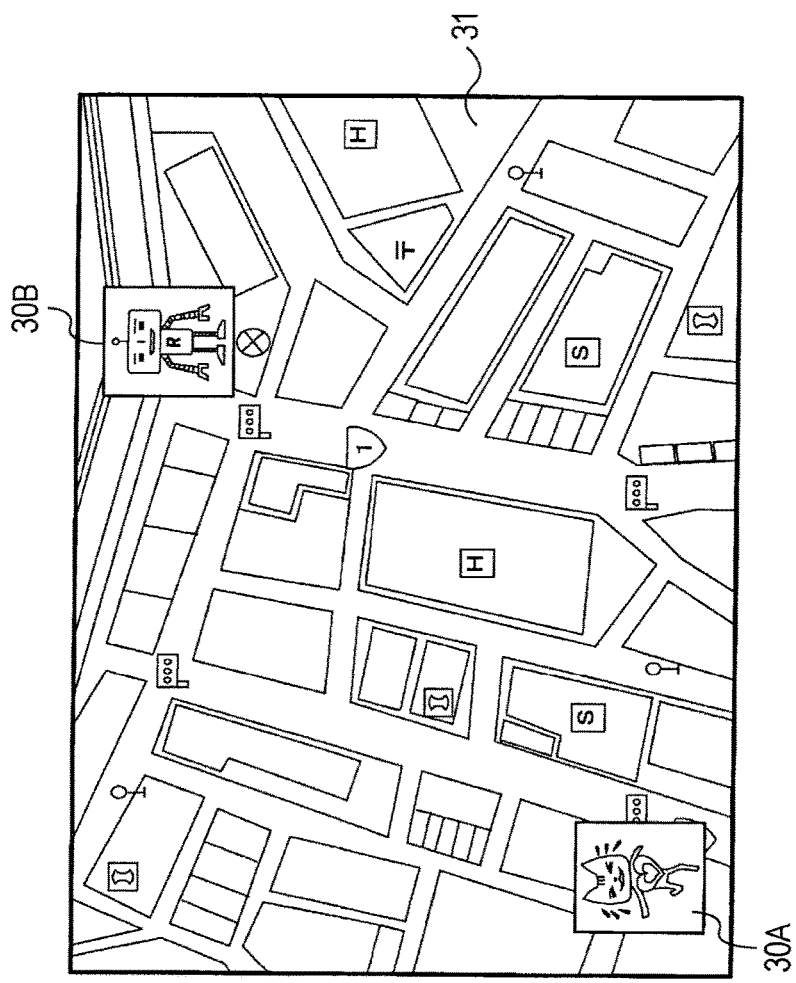
FIG. 18 is an illustration of an example of displayed avatars of a user and another person.

In the example shown in FIG. 18, for example, the state of the user of the information display apparatus 1, who is waiting for another person at the place of appointment, is represented by indicating the position of the user on the map image 31 and displaying the avatar 30B representing the user's state. In addition, the state of the other person who is late for the appointment and is thus running is displayed using the avatar 30A at the current position.

4. Advantages and Modifications of Embodiment

According to the above-described embodiment, the user of the information display apparatus 1 (or the display apparatus 200) can recognize the state of the user or another person from the expression or movement of an avatar. Accordingly, the user can be informed of the state of the user or another person with ease and delight.

For example, when an avatar representing the user's state is displayed, the user can enjoy the display screen or be informed of the precise state, such as tired or depressed, so that the user can pay attention to the user's subsequent behavior.

When the user's past state is displayed using an avatar, the user can precisely remember the user's behavior and emotions and can enjoy the user's memory.

When another person's state is displayed using an avatar, the user can be informed of the precise state of the other person.

For example, the user can be informed of the state and the current position of the user's friend who is late for an appointment with the user. In addition, the parents of a child can be informed of the current place and position where the child is. Further, the state of an unhealthy person who is away from home can be easily checked by his or her family. In this manner, various applications are conceivable.

The present invention is not limited to the above-described embodiment, and various modifications can be made as exemplary structures of the apparatuses and exemplary processes.

The foregoing structures of the information display apparatus 1, the transmitting apparatus 100, the display apparatus 200, and the server apparatus 70 are only examples, and additions and deletions of various structural elements can be made in accordance with the actually implemented operations and functions.

In the information processing system shown in FIG. 9, the display apparatus 200 obtains bio-information and the like detected by the transmitting apparatus 100 via the server apparatus 70. Alternatively, a system configuration including no server apparatus 70 is conceivable. That is, in a system in which the transmitting apparatus 100 and the display apparatus 200 directly communicate with each other, the display apparatus 200 can receive bio-information, kinetic information, position information, and the like detected by the transmitting apparatus 100 and display an avatar based on another person's bio- and kinetic information or the avatar on a map using the position information.

The information display apparatus 1 and the display apparatus 200 each include the display unit 14 (214). Alternatively, the information display apparatus 1 and the display apparatus 200 may include no display unit and may display an avatar using another independent display device.

With regard to displaying an avatar of another person based on this person's bio- and kinetic information and the position of this person based on this person's position information, it is appropriate to impose some limits in order to protect this person's privacy.

For example, when the user of the display apparatus 200 requests to display an avatar and the current position of the user of the transmitting apparatus 100, the server apparatus 70 asks the user of the transmitting apparatus 100 to agree to display his or her avatar and current position. Only when the user of the transmitting apparatus 100 agrees to do so, the server apparatus 70 transmits bio-information and avatar-related information to the display apparatus 200.

Further, when detected bio-information which is the heart rate, blood pressure, or the like shows a normal value, the bio-information may not be used to display an avatar. Only when the detected bio-information shows a physically abnormal value, the bio-information may be used to display an avatar. Accordingly, an avatar serving as a warning or alert to the user or another person may be displayed.

By constructing the transmitting apparatus 100 to be wearable by a living body other than a human being, such as a pet, e.g., a dog or a cat, the pet can serve as a subject, and its bio-information, kinetic information, and position information can be detected. In this case, the user of the display apparatus 200 can check the pet's state using an avatar.

It should be understood by those skilled in the art that various modifications, combinations, sub-combinations and alterations may occur depending on design requirements and other factors insofar as they are within the scope of the appended claims or the equivalents thereof.

What is claimed is:

1. An information processing method, the method comprising:
    receiving kinetic information of a subject;
    determining a state of the subject based on the received kinetic information;
    performing a control operation using a controller to determine a figure of the subject and subsequently change a representation of the figure to indicate the state of the subject; and
    simultaneously displaying, on a map, the figure and position information regarding the subject to a person.

2. The information processing method of claim 1, wherein the method further comprises controlling display, on the map, of the figure at a position corresponding to a position of the subject.

3. The information processing method of claim 1, wherein the method further comprises displaying, on the map, a second figure representing a second subject different than the subject, wherein the second figure indicates a state of the second subject.

4. The information processing method of claim 1, wherein the method further comprises displaying, on the map, time information regarding the subject.

5. The information processing method of claim 1, wherein the method further comprises controlling provision of state history of the subject.

6. The information processing method of claim 1, wherein the method further comprises:
    receiving updated kinetic information of the subject;
    determining an updated state of the subject based on the updated kinetic information; and
    performing a control operation using the controller to change the figure indicating the state of the subject to a figure indicating the updated state of the subject.

7. An information processing apparatus comprising:
    circuitry configured to:
        receive kinetic information of a subject;
        determine a state of the subject based on the received kinetic information;
        perform a control operation using a controller to determine a figure of the subject and subsequently change a representation of the figure to indicate the state of the subject; and
        simultaneously display, on a map, the figure and position information regarding the subject to a person.

8. The information processing apparatus of claim 7, wherein the circuitry is further configured to control display, on the map, of the figure at a position corresponding to a position of the subject.

9. The information processing apparatus of claim 7, wherein the circuitry is further configured to display, on the map, a second figure representing a second subject different than the subject, wherein the second figure indicates a state of the second subject.

10. The information processing apparatus of claim 7, wherein the circuitry is further configured to display, on the map, time information regarding the subject.

11. The information processing apparatus of claim 7, wherein the circuitry is further configured to control provision of state history of the subject.

12. The information processing apparatus of claim 7, wherein the circuitry is further configured to:
    receive updated kinetic information of the subject;
    determine an updated state of the subject based on the updated kinetic information; and
    perform a control operation using the controller to change the figure indicating the state of the subject to a figure indicating the updated state of the subject.

13. A non-transitory computer readable medium having encoded thereon executable instructions that, when executed by at least one processor, perform a method comprising:
    receiving kinetic information of a subject;

determining a state of the subject based on the received kinetic information;

performing a control operation using a controller to determine a figure of the subject and subsequently change a representation of the figure to indicate the state of the subject; and simultaneously displaying, on a map, the figure and position information regarding the subject to a person.

14. The non-transitory computer readable medium of claim 13, wherein the method further comprises controlling display, on the map, of the figure at a position corresponding to a position of the subject.

15. The non-transitory computer readable medium of claim 13, wherein the method further comprises displaying, on the map, a second figure representing a second subject different than the subject, wherein the second figure indicates a state of the second subject.

16. The non-transitory computer readable medium of claim 13, wherein the method further comprises displaying, on the map, time information regarding the subject.

17. The non-transitory computer readable medium of claim 13, wherein the method further comprises controlling provision of state history of the subject.

\* \* \* \* \*